United States Patent
Makifuchi

(10) Patent No.: US 10,140,697 B2
(45) Date of Patent: *Nov. 27, 2018

(54) RADIATION IMAGING SYSTEM AND IMAGE PROCESSING DEVICE

(71) Applicant: Konica Minolta, Inc., Chiyoda-ku, Tokyo (JP)

(72) Inventor: Chiho Makifuchi, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/801,757

(22) Filed: Nov. 2, 2017

(65) Prior Publication Data

US 2018/0144456 A1    May 24, 2018

Related U.S. Application Data

(63) Continuation of application No. 15/192,201, filed on Jun. 24, 2016, now Pat. No. 9,870,610.

(30) Foreign Application Priority Data

Jun. 26, 2015    (JP) .................................. 2015-128503

(51) Int. Cl.
   *G06K 9/00* (2006.01)
   *G06T 7/00* (2017.01)
   *G06T 11/00* (2006.01)
   *A61B 6/00* (2006.01)

(52) U.S. Cl.
   CPC .......... *G06T 7/0002* (2013.01); *A61B 6/4291* (2013.01); *A61B 6/484* (2013.01); *A61B 6/505* (2013.01); *A61B 6/5211* (2013.01); *A61B 6/5264* (2013.01); *G06T 11/005* (2013.01); *A61B 6/5205* (2013.01); *G06T 2207/10116* (2013.01); *G06T 2207/30008* (2013.01); *G06T 2207/30168* (2013.01)

(58) Field of Classification Search
   None
   See application file for complete search history.

(56) References Cited

U.S. PATENT DOCUMENTS 6,639,685 B1    10/2003    Gu et al.

FOREIGN PATENT DOCUMENTS

| | | |
|---|---|---|
| JP | 2011206162 A | 10/2011 |
| JP | 2011206188 A | 10/2011 |

*Primary Examiner* — Atiba O Fitzpatrick
(74) *Attorney, Agent, or Firm* — Cantor Colburn LLP

(57) ABSTRACT

A radiation imaging system includes a radiation imaging device, a reconstruction unit and a detection unit. The reconstruction unit generates at least two of a differential phase image, an absorption image and a small-angle scattering image based on periodic pattern images of a subject obtained by the imaging device. The detection unit performs regression analysis on at least two images of (a) the differential phase image, a differential absorption image of the absorption image and a differential small-angle scattering image of the small-angle scattering image or (b) a phase image of the differential phase image, the absorption image and the small-angle scattering image; calculates a value of an indicator indicating a relationship between the at least two images; and detects image quality deterioration due to change in relative position of the imaging device and the subject based on the value.

10 Claims, 16 Drawing Sheets

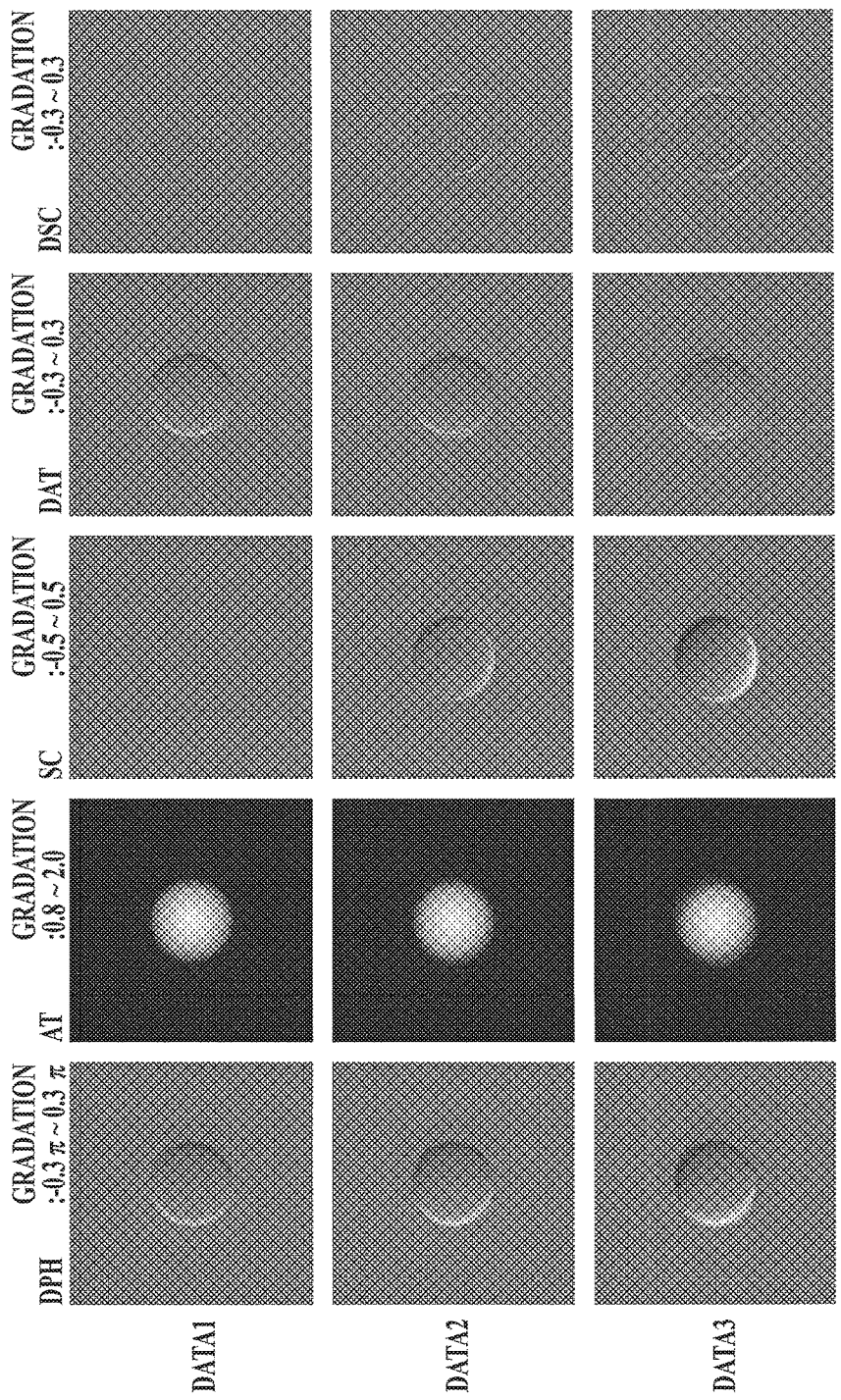

FIG. 13

| | SET1 | SET2 | SET3 | SET4 | SET5 | SET6 | SET7 | SET8 | SET9 |
|---|---|---|---|---|---|---|---|---|---|
| GRATING POSITION 1 | SET1_1 | SET2_1 | SET3_1 | SET4_1 | SET2_1 | SET1_1 | SET1_1 | SET1_1 | SET1_1 |
| GRATING POSITION 2 | SET1_2 | SET2_2 | SET3_2 | SET4_2 | SET1_2 | SET2_2 | SET1_2 | SET1_2 | SET2_2 |
| GRATING POSITION 3 | SET1_3 | SET2_3 | SET3_3 | SET4_3 | SET1_3 | SET1_3 | SET2_3 | SET1_3 | SET3_3 |
| GRATING POSITION 4 | SET1_4 | SET2_4 | SET3_4 | SET4_4 | SET1_4 | SET1_4 | SET1_4 | SET2_4 | SET4_4 |

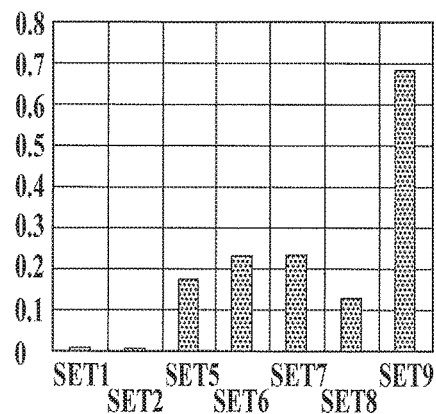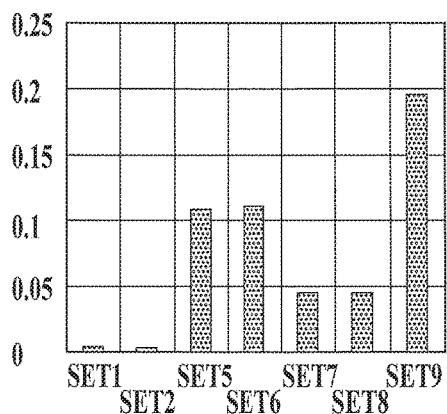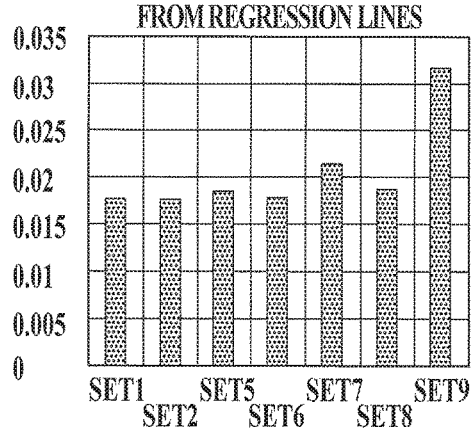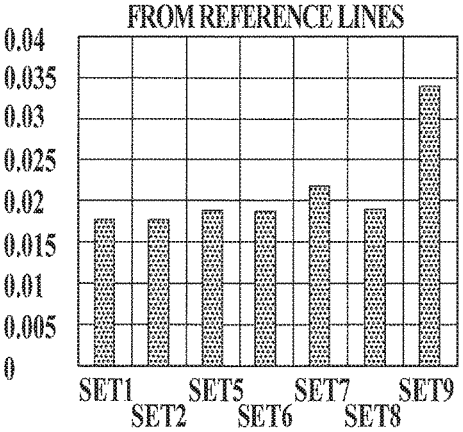

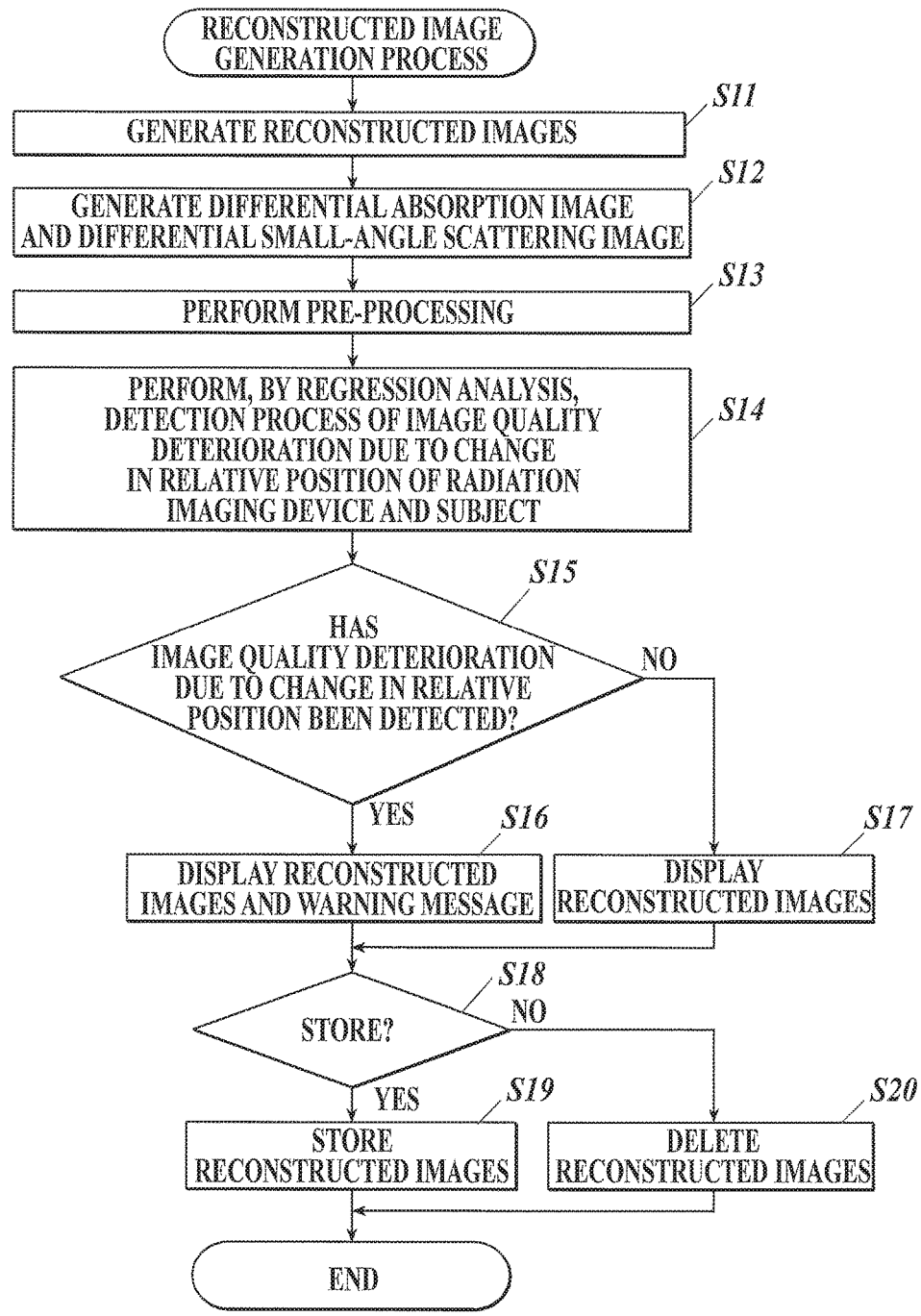

RADIATION IMAGING SYSTEM AND IMAGE PROCESSING DEVICE

CROSS-REFERENCE TO RELATED APPLICATIONS

The present invention is a continuation of U.S. application Ser. No. 15/192,201, filed on Jun. 24, 2016, and is based upon and claims a priority under the Paris Convention of Japanese Patent Application No. 2015-128503 filed on Jun. 26, 2015, the entire disclosure of which, including the specification, claims, drawings and abstract, is incorporated herein by reference in its entirety.

FIELD OF THE INVENTION

The present invention relates to a radiation imaging system and an image processing device.

DESCRIPTION OF THE RELATED ART

A radiation imaging device with a Talbot interferometer or Talbot-Lau interferometer employs a fringe scanning method to obtain high-resolution images. The fringe scanning method is a method of performing imaging M times (M is a positive integer of more than 2) while moving one of gratings 1/M of a slit interval of the grating for each imaging in a slit interval direction, thereby obtaining images (moire images) for reconstruction.

However, if relative position (positional relationship) of the radiation imaging device and a subject changes while the radiation imaging device is taking M moire images by imaging of fringe scanning, physical quantities determined by the imaging may contain errors, and image quality deterioration may occur in a reconstructed image(s), which is generated by reconstruction of M moire images. Such a situation is not preferred.

Then, there is described, for example, in Patent Document 1 (Japanese Patent Application Publication No. 2011-206162) and Patent Document 2 (Japanese Patent Application Publication No. 2011-206188) a technology of detecting the amount of movement (moving amount) of a subject by imaging the subject, to the surface of which a marker or the like is attached.

In the technology described in Patent Documents 1 and 2, movement of a subject (subject movement) is detected by making use of change in position or intensity of pixels onto which a maker attached to the surface of the subject is projected. Hence, subject movement cannot be accurately detected if, for example, the subject moves three-dimensionally (rotates or moves in an emission axis direction of radiation); a part where the marker is disposed and a part where the marker is not disposed move differently; or the surface of the subject and the inside of the subject move differently.

Further, although it is good if an operator can judge image quality deterioration due to change in relative position of the radiation imaging device and a subject from a reconstructed image(s) or moire images, it is difficult to accurately judge change in signal(s) due to movement of the radiation imaging device or the subject unless the radiation imaging device or the subject largely moves and strong artifacts appear. For example, in medical use, if a target of interest is not captured in an image, its cause/reason cannot be identified; for example, the cause/reason may be no existence of the target from the beginning, image quality deterioration due to movement of the radiation imaging device or the patient, wrong positioning of the patient, or other error originated from the device or the like. This leads to misdiagnosis or excessive exposure to radiation due to unnecessary re-imaging (re-fringe scanning). Similarly, in industrial use too, the above leads to a wrong examination result or excessive examination time.

BRIEF SUMMARY OF THE INVENTION

Objects of the present invention include detecting image quality deterioration due to change in relative position of a radiation imaging device and a subject from image data without using a special tool such as a marker.

In order to achieve at least one of the objects, according to a first aspect of the present invention, there is provided a radiation imaging system including: a radiation imaging device which includes at least one grating provided in an emission axis direction of radiation and obtains a plurality of periodic pattern images by performing fringe scanning with a subject placed at a subject placement position provided on an emission path of the radiation while moving the grating; and an image processing device including: a reconstruction unit which generates at least two reconstructed images of a differential phase image, an absorption image and a small-angle scattering image based on the periodic pattern images; and a detection unit which (i) performs regression analysis on signal values of at least two images of (a) the differential phase image, a differential absorption image generated by differentiating the absorption image, and a differential small-angle scattering image generated by differentiating the small-angle scattering image, or (b) a phase image generated by integrating the differential phase image, the absorption image, and the small-angle scattering image, the at least two images being a target of the regression analysis, (ii) calculates an indicator value of an indicator indicating a relationship between the at least two images, and (iii) detects image quality deterioration due to change in relative position of the radiation imaging device and the subject based on the calculated indicator value.

Further, according to a second aspect of the present invention, there is provided an image processing device which performs image processing on a plurality of periodic pattern images obtained by a radiation imaging device which includes at least one grating provided in an emission axis direction of radiation performing fringe scanning with a subject placed at a subject placement position provided on an emission path of the radiation while moving the grating, the image processing device including: a reconstruction unit which generates at least two reconstructed images of a differential phase image, an absorption image and a small-angle scattering image based on the periodic pattern images; and a detection unit which (i) performs regression analysis on signal values of at least two images of (a) the differential phase image, a differential absorption image generated by differentiating the absorption image, and a differential small-angle scattering image generated by differentiating the small-angle scattering image, or (b) a phase image generated by integrating the differential phase image, the absorption image, and the small-angle scattering image, (ii) calculates an indicator value of an indicator indicating a relationship between the at least two images, and (iii) detects image quality deterioration due to change in relative position of the radiation imaging device and the subject based on the calculated indicator value.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein:

FIG. 8 shows images generated by simulating a case where a subject does not move (DATA1) and a case where the subject moves (DATA2 and DATA3);

FIG. 13 shows combinations of positions of a subject (subject positions) in generating moire images in an experiment;

FIG. 16A is a graph of the root mean square of differences between references a1 and slopes a1;

FIG. 16B is a graph of the root mean square of differences between references R2 and the coefficients of determination R2;

FIG. 16C is a graph of the root mean square of the standard deviations σ of the image data from the regression lines;

FIG. 16D is a graph of the root mean square of the standard deviations σ of the image data from the reference lines;

FIG. 18 is a flowchart of a reconstructed image generation process performed by a control unit shown in FIG. 4.

DETAILED DESCRIPTION OF THE INVENTION

In an embodiment below, the present invention is applied to a radiation imaging system using a Talbot-Lau interferometer. However, the present invention is not limited to one using a Talbot-Lau interferometer and hence is applicable to any radiation imaging system which uses at least a first grating, takes a plurality of periodic pattern images based on projection of the first grating or radiation intensity modulated by Talbot effect, and obtains at least two of a differential phase image, a small-angle scattering image and an adsorption image by calculation based on the principles of fringe scanning.

Hereinafter, an embodiment of the present invention is described with reference to the drawings.

Figure 1:
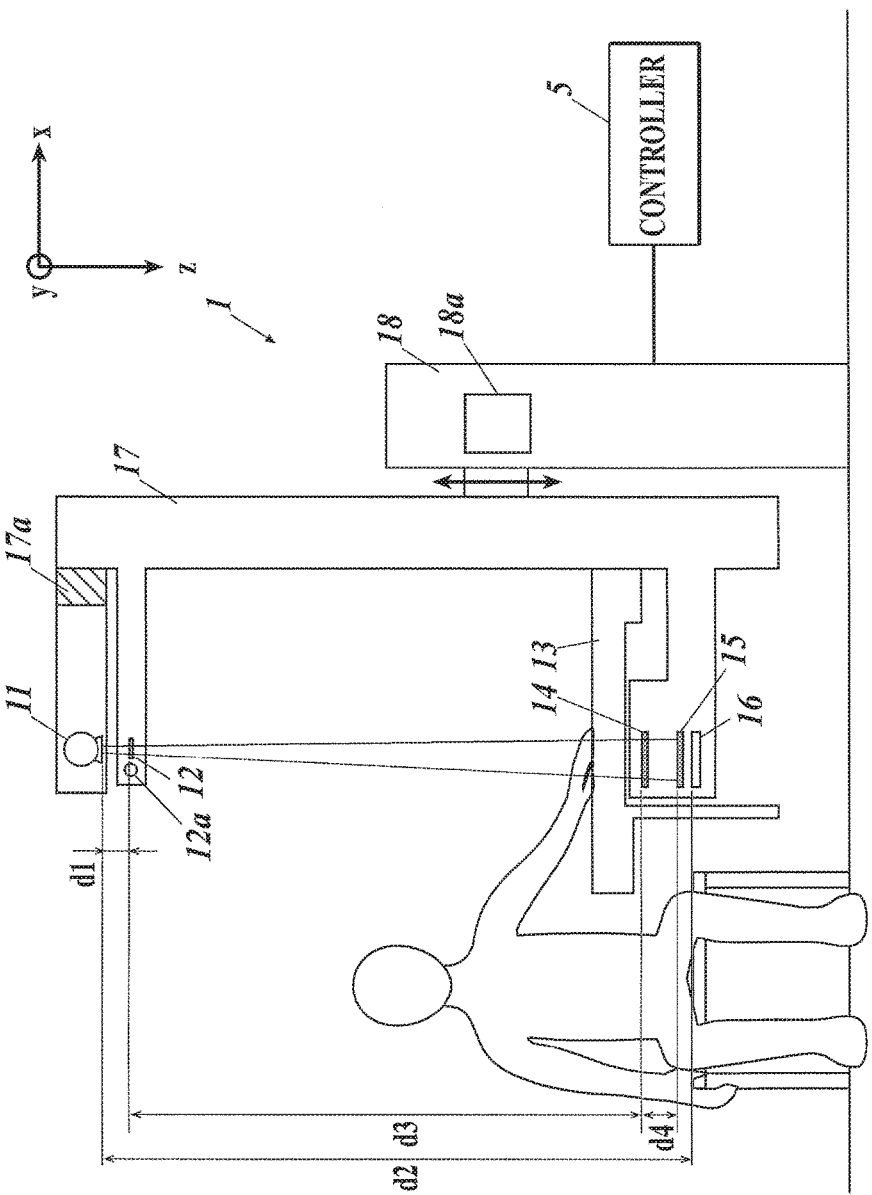
FIG. 1 shows the overall configuration of a radiation imaging system according to an embodiment of the present invention.

FIG. 1 shows a radiation imaging system according to an embodiment of the present invention. The radiation imaging system includes a radiation imaging device 1 and a controller 5. The radiation imaging device 1 performs X-ray imaging (fringe scanning) with a Talbot-Lau interferometer, and the controller 5 generates reconstructed images of a subject using a plurality of moire images obtained by the X-ray imaging. In the embodiment, the radiation imaging system performs imaging using X-rays, but may use other radiation, for example, gamma rays.

The radiation imaging device 1 includes, as shown in FIG. 1, a radiation source 11, a multi-slit 12, a subject table 13, a first grating 14, a second grating 15, a radiation detector 16, a support unit 17 and a main body unit 18.

The radiation imaging device 1 is a vertical type, and the radiation source 11, the multi-slit 12, the subject table 13, the first grating 14, the second grating 15 and the radiation detector 16 are arranged in this order in a Z direction which is the gravity direction. In FIG. 1, d1 (mm) represents distance between the focal point of the radiation source 11 and the multi-slit 12, d2 (mm) represents distance between the focal point of the radiation source 11 and the radiation detector 16, d3 (mm) represents distance between the multi-slit 12 and the first grating 14, and d4 (mm) represents distance between the first grating 14 and the second grating 15. The subject table 13 may be positioned between the first grating 14 and the second grating 15.

The distance d1 is preferably 5 mm to 500 mm and far preferably 5 mm to 300 mm.

The distance d2 is preferably 3,000 mm or less because the height of an imaging room is about 3 m or less in general. The distance d2 is far preferably 400 mm to 3,000 mm and still far preferably 500 mm to 2,000 mm.

The distance (d1+d3) between the focal point of the radiation source 11 and the first grating 14 is preferably 300 mm to 3,000 mm and far preferably 400 mm to 1,800 mm.

The distance (d1+d3+d4) between the focal point of the radiation source 11 and the second grating 15 is preferably 400 mm to 3,000 mm and far preferably 500 mm to 2,000 mm.

As these distances, optimum distances with which a grating image (self-image) of the first grating 14 lies on the second grating 15 may be calculated and set from: the wavelength of X-rays emitted from the radiation source 11; the slit interval of the first grating 14; and the slit interval of the second grating 15.

The radiation source 11, the multi-slit 12, the subject table 13, the first grating 14, the second grating 15 and the radiation detector 16 are all supported by the support unit 17, and a positional relationship thereof in the z direction is fixed. The support unit 17 is formed to be arm-shaped and attached to the main body unit 18 to be movable in the z direction through a drive unit 18a provided in the main body unit 18.

The radiation source 11 is supported through a buffer member 17a. The buffer member 17a may be formed of any material as long as it can absorb shocks and vibrations. Examples thereof include an elastomer. The radiation source 11 emits X-rays and thereby generates heat. Hence, the material of a part of the buffer member 17a, the part being close to the radiation source 11, is preferably heat-insulating too.

The radiation source 11 includes an X-ray tube, and generates X-rays with the X-ray tube and emits the X-rays in the gravity direction (z direction). As the X-ray tube, for example, a Coolidge X-ray tube or a rotating anode X-ray tube widely and generally used at medical scenes can be used. For the anode, tungsten or molybdenum can be used.

The diameter of the focal point of the radiation source 11 (X-ray tube) is preferably 0.03 mm to 3 mm and far preferably 0.1 mm to 1 mm.

In the X-ray emission direction of the radiation source 11, a not-shown irradiation field diaphragm to narrow an irradiated area with X-rays is provided.

Figure 2:
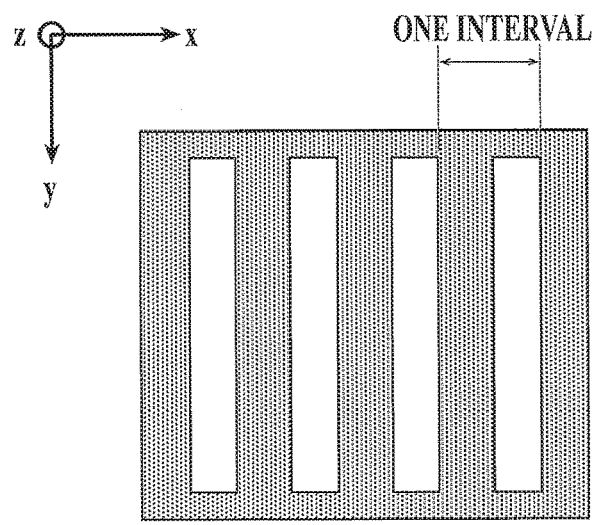
FIG. 2 is a plane view of a multi-slit.

The multi-slit 12 (third grating) is a diffraction grating in which slits are arranged at predetermined intervals in an x direction as shown in FIG. 2. The multi-slit 12 is formed of a material having a large X-ray shielding force, namely, a material having a high X-ray absorption factor, such as tungsten, lead or gold, on a substrate formed of a material having a low X-ray absorption factor, such as silicon or glass. The multi-slit 12 is formed, for example, by using photolithography by which a resist layer is masked in the shape of slits and irradiated with UV, so that the slit pattern is transferred to the resist layer. The slit structure having the same shape as the pattern is obtained by exposure, and metal is embedded in the slit structure by electroforming. Thus, the multi-slit 12 is formed.

The slit interval of the multi-slit 12 is 1 µm to 60 µm. The slit interval (one interval) is, as shown in FIG. 2, distance between slits adjacent to each other. The slit width (length in the x direction) is 1% to 60% of the slit interval, preferably 10% to 40% thereof. The slit height (length in the z direction) is 1 µm to 500 µm, preferably 1 µm to 150 µm.

The slit interval of the multi-slit 12 can be obtained by the following formula, wherein w0 (µm) represents the slit interval of the multi-slit 12, and w1 (µm) represents the slit interval of the first grating 14.

$$w0 = w1 \cdot (d3+d4)/d4$$

By determining the slit interval w0 in such a way as to satisfy the formula, self-images formed by X-rays having passed through the slits of the multi-slit 12 and the first grating 14 are superimposed on the second grating 15. This state is what is called "in focus".

As shown in FIG. 1, adjacent to the multi-slit 12, a drive unit 12a is provided. The drive unit 12a moves the multi-slit 12 in the x direction which is at right angles to the z direction. As the drive unit 12a, a drive mechanism(s) having a relatively large speed reduction ratio, such as a worm gear speed reducer, can be used alone or in combination.

The subject table 13 is where a subject is placed, and provided at a subject placement position on a path of X-rays (an emission path of radiation) emitted from the radiation source 11.

The first grating 14 is, as with the multi-slit 12, a diffraction grating in which slits are arranged at predetermined intervals in the x direction (see FIG. 2). The first grating 14 can be formed by photolithography with UV as with the multi-slit 12 or may be formed by what is called ICP by which a silicon substrate is deeply grooved with fine lines, whereby the grating structure is formed of silicon only. The slit interval of the first grating 14 is 1 µm to 20 µm. The slit width is 20% to 70% of the slit interval, preferably 35% to 60% thereof. The slit height is 1 µm to 100 µm.

In the case where the first grating 14 used is a phase grating, the slit height is made to be a height with which phase difference due to two types of materials forming the slit interval, namely, a material of an X-ray transmitting part and a material of an X-ray shielding part, becomes $\pi/8$ to $15 \times \pi/8$, preferably $\pi/2$ or $\pi$. In the case where the first grating 14 used is an absorption grating, the slit height is made to be a height with which the X-ray shielding part sufficiently absorbs X-rays.

In the case where the first grating 14 used is the phase grating having a phase difference due to the material of the X-ray transmitting part and the material of the X-ray shielding part of $\pi/2$, the distance d4 between the first grating 14 and the second grating 15 needs to substantially satisfy the following condition.

$$d4 = (m+\tfrac{1}{2}) \cdot w12/\lambda$$

In the above, m represents an integer, and λ represents the wavelength of X-rays.

The second grating 15 is, as with the multi-slit 12, a diffraction grating in which slits are arranged at predetermined intervals in the x direction (see FIG. 2). The second grating 15 can also be formed by photolithography. The slit interval of the second grating 15 is 1 µm to 20 µm. The slit width is 30% to 70% of the slit interval, preferably 35% to 60% thereof. The slit height is 1 µm to 100 µm.

In the embodiment, the grating planes of the first grating 14 and the second grating 15 are perpendicular to the z direction (parallel in the x-y plane). The slit direction of the first grating 14 and the slit direction of the second grating 15 are arranged to (slightly) incline at a predetermined angle in the x-y plane, but they may be arranged parallel.

The multi-slit 12, the first grating 14 and the second grating 15 can be configured, for example, as written below.

Radiation Source 11: Diameter of Focal Point; 300 µm, Tube Voltage; 40 kVp,

Added Filter; aluminum and 1.6 mm

Distance d1 from Focal Point of Radiation Source 11 to Multi-slit 12: 240 mm

Distance d3 from Multi-slit 12 to First Grating 14: 1,110 mm

Distance d3+d4 from Multi-slit 12 to Second Grating 15: 1,370 mm

Multi-slit 12: Size; 10 mm square, Slit Interval; 22.8 μm

First Grating 14: Size; 50 mm square, Slit Interval; 4.3 μm

Second Grating 15: Size; 50 mm square, Slit Interval; 5.3 μm

In the radiation detector 16, conversion elements which generate electric signals according to the amounts of X-rays with which the conversion elements are irradiated are two-dimensionally arranged. The radiation detector 16 reads the electric signals generated by the conversion elements as image signals.

The pixel size of the radiation detector 16 is preferably 10 μm to 300 μm and far preferably 50 μm to 200 μm.

It is preferable that the radiation detector 16 be fixed to the support unit 17 in such a way as to contact the second grating 15. This is because, the larger the distance between the second grating 15 and the radiation detector 16 is, the more the moire images obtained by the radiation detector 16 are blurred.

As the radiation detector 16, an FPD (Flat Panel Detector) can be used. There are an indirect conversion type FPD, which detects X-rays and converts the detected X-rays into electric signals through photo-electric conversion elements, and a direct conversion type FPD, which detects X-rays and directly converts the detected X-rays into electric signals. Either of them can be used.

The indirect conversion type FPD is configured in such a way that, under a scintillator plate made of CsI, Gd2O2S or the like, photo-electric conversion elements associating with TFTs (Thin Film Transistors) are two-dimensionally arranged, thereby constituting pixels. When absorbs X-rays entering the radiation detector 16, the scintillator plate emits light. The photo-electric conversion elements convert this emitted light into electric charges and accumulate the electric charges therein. The accumulated electric charges are read out as image signals.

The direct conversion type FPD is configured in such a way that an amorphous selenium film, having a film thickness of 100 μm to 1,000 μm, is formed on glass by thermal deposition of amorphous selenium, and the amorphous selenium film and electrodes are vapor-deposited on an array of TFTs which are two-dimensionally arranged. When the amorphous selenium film absorbs X-rays, voltage is released into the substance in the form of electron-hole pairs, and the TFTs read out voltage signals between the electrodes.

As the radiation detector 16, an imager such as a CCD (Charge Coupled Device) or an X-ray camera may be used.

The radiation detector 16 may be provided with not the second grating 15 but the intensity modulation effect of the second grating 15. In this case, in order to provide the scintillator with a dead region(s) with the same slit interval and slit width as those of the second grating 15, the scintillator may be grooved to be grating-shaped (Reference Document 1: Japanese Patent No. 5,127,246).

Figure 3:
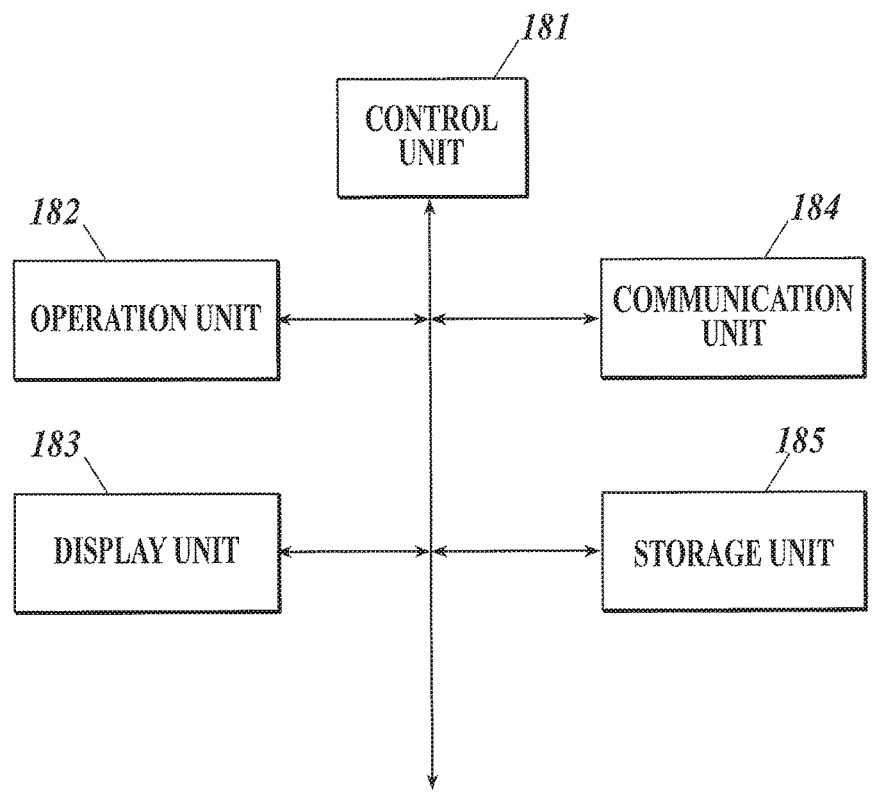
FIG. 3 is a block diagram showing the functional configuration of a main body unit shown in FIG. 1.

The main body unit 18 includes, as shown in FIG. 3, a control unit 181, an operation unit 182, a display unit 183, a communication unit 184 and a storage unit 185.

The control unit 181 includes a CPU (Central Processing Unit) and a RAM (Random Access Memory) and performs various processes in cooperation with programs stored in the storage unit 185. The control unit 181 is connected with the units such as the radiation source 11, the drive unit 12a, the drive unit 18a and the radiation detector 16 and controls, by performing the below-described imaging control process or the like, for example, timing of and conditions for emitting X-rays (X-ray emission conditions) from the radiation source 11, timing of reading image signals with the radiation detector 16 and movement of the multi-slit 12 according to setting information on imaging conditions input from the controller 5.

The operation unit 182 includes an exposure switch, and generates operation signals in response to the exposure switch and so forth being operated and outputs the operation signals to the control unit 181.

The display unit 183 displays, on its display, operation screens, action statuses of the radiation imaging device 1 and so forth under the display control of the control unit 181.

The communication unit 184 includes a communication interface and communicates with the controller 5 on a network. For example, the communication unit 184 sends moire images to the controller 5, the moire images being read by the radiation detector 16 and stored in the storage unit 185.

The storage unit 185 stores therein programs which are executed by the control unit 181 and data necessary for execution of the programs. The storage unit 185 also stores therein moire images obtained by the radiation detector 16.

In the embodiment, the radiation imaging device 1 is a vertical type, but may be a horizontal type or an oblique type. Further, the radiation source 11, the multi-slit 12, the subject table 13, the first grating 14, the second grating 15 and the radiation detector 16 may be arranged in order to be opposite to gravity.

The controller 5 controls an imaging action of the radiation imaging device 1 in response to operator operations. Further, the controller 5, which serves as an image processing device, performs image processing on a series of moire images obtained by the radiation imaging device 1. For example, the controller 5 generates reconstructed images (an absorption image, a small-angle scattering image and a differential phase image) of a subject, using a series of moire images obtained by the radiation imaging device 1.

Figure 4:
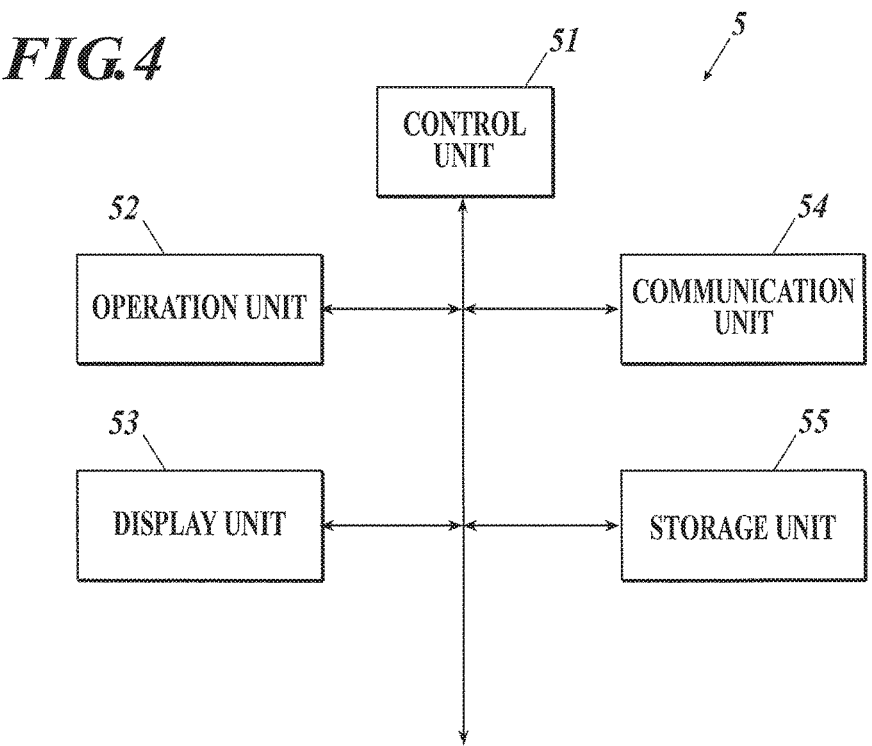
FIG. 4 is a block diagram showing the functional configuration of a controller shown in FIG. 1.

The controller 5 includes, as shown in FIG. 4, a control unit 51, an operation unit 52, a display unit 53, a communication unit 54 and a storage unit 55.

The control unit 51 includes a CPU (Central Processing Unit) and a RAM (Random Access Memory) and performs various processes including the below-described reconstructed image generation process with programs stored in the storage unit 55. The control unit 51 functions as a detection unit, an extraction unit, a pre-processing unit and a noise pixel extraction unit.

The operation unit 52 includes: a keyboard provided with cursor keys, number input keys, various function keys and so forth; and a pointing device such as a mouse, and generates press signals in response to the keys of the keyboard being pressed and operation signals in response to the mouse being operated and outputs the press signals and the operation signals to the control unit 51 as input signals. The operation unit 52 may also include a touch panel integrated into a display of the display unit 53, and generate operation signals in response to the touch panel being operated and output the operation signals to the control unit 51.

The display unit 53 includes a monitor such as a CRT (Cathode Ray Tube) or an LCD (Liquid Crystal Display) and displays operation screens, a message to warn (warning message) that image quality deterioration due to change in relative position of the radiation imaging device 1 and a subject has been detected and so forth under the display control of the control unit 51. The display unit 53 functions as an output unit.

The communication unit 54 includes a communication interface and communicates with the radiation imaging device 1 or the radiation detector 16 on a network with or without a cable. For example, the communication unit 54 sends imaging conditions and control signals to the radiation imaging device 1 and receives moire images from the radiation imaging device 1 or the radiation detector 16.

The storage unit 55 stores therein programs which are executed by the control unit 51 and data necessary for execution of the programs. For example, the storage unit 55 stores therein imaging order information which is information on imaging (fringe scanning) booked by a not-shown RIS (Radiology Information System), HIS (Hospital Information System) or the like. The imaging order information includes: patient information such as a patient ID and a patient name; and imaging site (subject site) information.

The storage unit 55 also stores therein an imaging condition table in which subject sites and imaging conditions suitable for the respective subject sites are correlated with each other.

The storage unit 55 also stores therein moire images obtained by the radiation imaging device 1 based on the imaging order information, reconstructed images generated based on the moire images, and so forth being correlated with the imaging order information.

The storage unit 55 also stores therein gain correction data, a defect pixel map and so forth for the radiation detector 16 in advance. The defect pixel map is positional information (coordinates) of defect pixels (missing pixels included) of the radiation detector 16.

The storage unit 55 also stores therein, as reference values, indicator values of indicators (e.g., a slope al) each of which indicates a relationship between images generated in a state in which change in relative position of the radiation imaging device 1 and a subject is not present, the indicator values being calculated in advance.

<Action of Radiation Imaging System>

Hereinafter, an X-ray imaging method with the Talbot-Lau interferometer of the radiation imaging device 1 is described.

Figure 5:
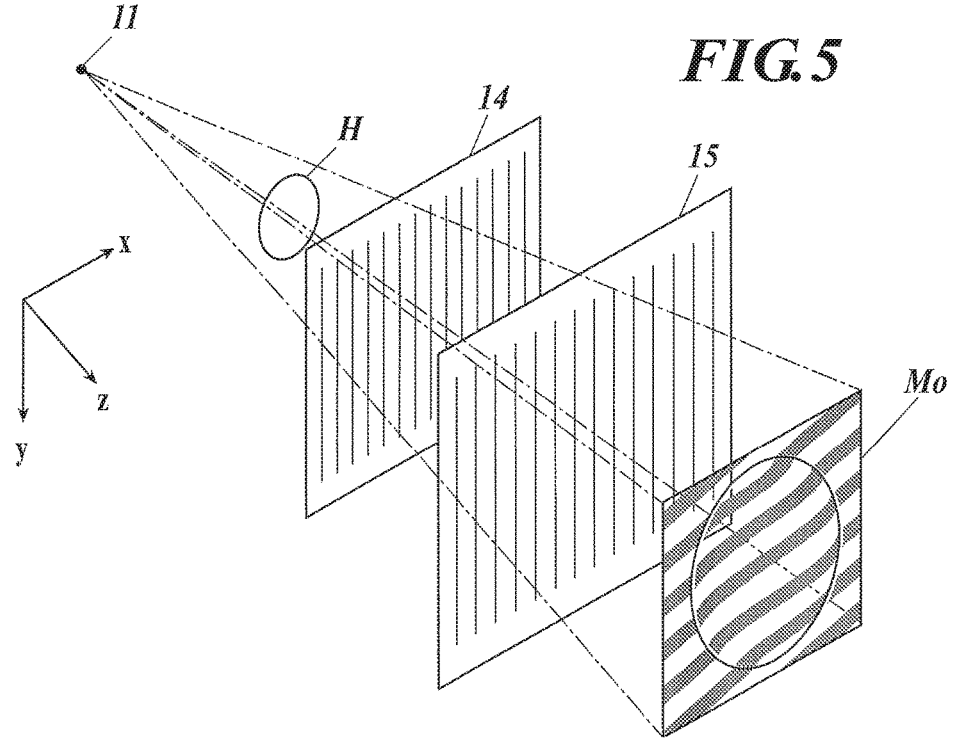
FIG. 5 is an illustration to explain principles of a Talbot interferometer.

As shown in FIG. 5, when X-rays emitted from the radiation source 11 pass through the first grating 14, the X-rays, which have passed through the first grating 14, form an image at constant intervals in the z-direction. These images are called self-images, and phenomenon of self-images being formed is called Talbot effect. The second grating 15 is arranged at a position where a self-image is formed, in such a way as to be approximately parallel to the self-image, and the X-rays having passed through the second grating 15 form a moire image ("Mo" in FIG. 5). That is, the first grating 14 forms a periodic pattern, and the second grating 15 converts the periodic pattern into moire fringes. When a subject ("H" in FIG. 5) exists between the radiation source 11 and the first grating 14, the phase of the X-rays is shifted by the subject, so that, as shown in FIG. 5, the moire fringes on the moire image are deformed with the periphery of the subject as a boundary. This deformation of the moire fringes is detected by processing the moire image, so that an image of the subject is formed. This is the principles of a Talbot interferometer. The above periodic pattern is not limited to moire fringes, and a self-image may be directly photographed, or shadow of the first grating 14 may be observed without using Talbot effect.

In the radiation imaging device 1, the multi-slit 12 is provided near the radiation source 11 between the radiation source 11 and the first grating 14, and X-ray imaging with a Talbot-Lau interferometer is performed. A Talbot interferometer is premised on the radiation source 11 being an ideal point source, but in actual imaging (fringe scanning), the radiation source 11 having a focal point of a large diameter to some extent is used. Then, through the multi-slit 12, the radiation source 11 acts like a plurality of point sources arranged in a row emitting X-rays. This is the X-ray imaging method with a Talbot-Lau interferometer. This method demonstrates the same Talbot effect as a Talbot interferometer even when the diameter of the focal point is large to some extent.

In the embodiment, imaging is performed with a method of fringe scanning. The fringe scanning means, in general, performing imaging M times (imaging of M steps) (M is a positive integer of more than 2) while moving one or two (the multi-slit 12 in the embodiment) of the gratings (the multi-slit 12, the first grating 14 and the second grating 15) in the slit interval direction (x direction) in relation to the other grating(s), thereby obtaining M moire images necessary to generate one reconstructed image. More specifically, (i) moving a grating(s) in the slit interval direction d/M (μm) and (ii) imaging are alternated, whereby M moire images are obtained, wherein d (μm) represents the slit interval of the grating(s) to be moved.

Figure 6:
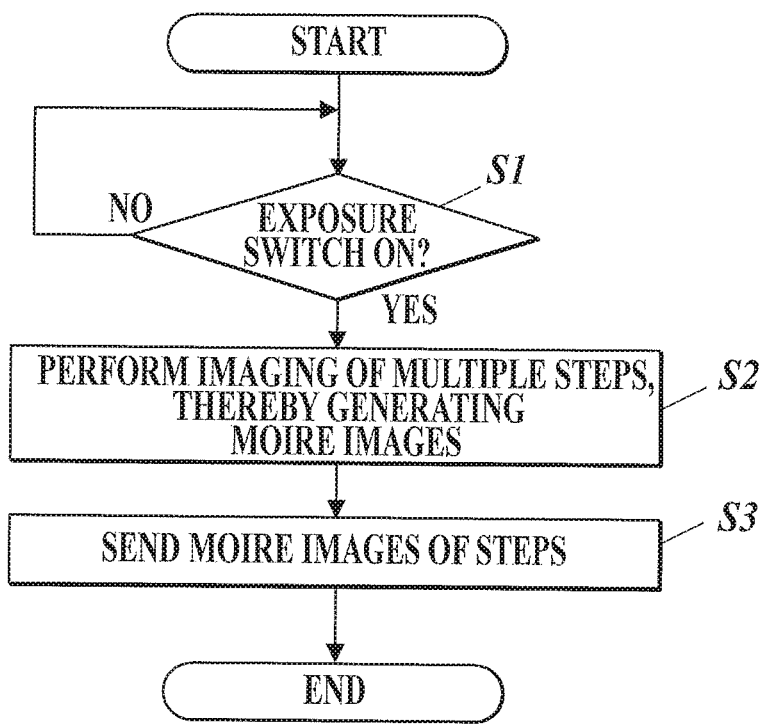
FIG. 6 is a flowchart of an imaging control process performed by a control unit shown in FIG. 3.

FIG. 6 is a flowchart of the imaging control process performed by the control unit 181 of the radiation imaging device 1. The flow of the imaging control process is described with reference to FIG. 6.

First, when an operator operates the exposure switch of the operation unit 182 (Step S1; YES), the control unit 181 controls the radiation source 11, the radiation detector 16 and the drive unit 12a so as to perform a series of imaging of a plurality of steps, thereby obtaining a series of moire images having different moire phases (Step S2).

In a series of imaging, first, the radiation source 11 starts emitting X-rays in a state in which the multi-slit 12 stops. In the radiation detector 16, after resetting is performed to remove unnecessary electric charges which have remained since the last imaging, electric charges are accumulated in response to the timing of the X-ray emission, and the accumulated electric charges are read as image signals in response to the timing of the stop of the X-ray emission. This is imaging of one step. At the timing when imaging of one step finishes, the multi-slit 12 starts moving. The multi-slit 12 stops moving when having moved a predetermined amount, and imaging of the next step is performed. Thus, the multi-slit 12 alternates moving with stopping a predetermined number of steps. When the multi-slit 12 stops, X-rays are emitted and image signals are read. The end of imaging with the multi-slit 12 having moved one interval of the slit interval means the end of a series of imaging to obtain a plurality of moire images necessary to generate one reconstructed image.

The number of steps M for a series of imaging is preferably 3 to 20 and far preferably 3 to 10. In order to obtain reconstructed images with high visibility in a short period of time, five steps are preferable (Reference Document 2: K. Hibino, B. F. Oreb and D. I. Farrant, Phase shifting for nonsinusoidal wave forms with phase-shift errors, J. Opt. Soc. Am. A, Vol. 12, 761-768 (1995), and Reference Document 3: A. Momose, W. Yashiro, Y. Takeda, Y. Suzuki and T. Hattori, Phase Tomography by X-ray Talbot Interferometry for biological imaging, Jpn. J. Appl. Phys., Vol. 45, 5254-5262 (2006)).

Figure 7:
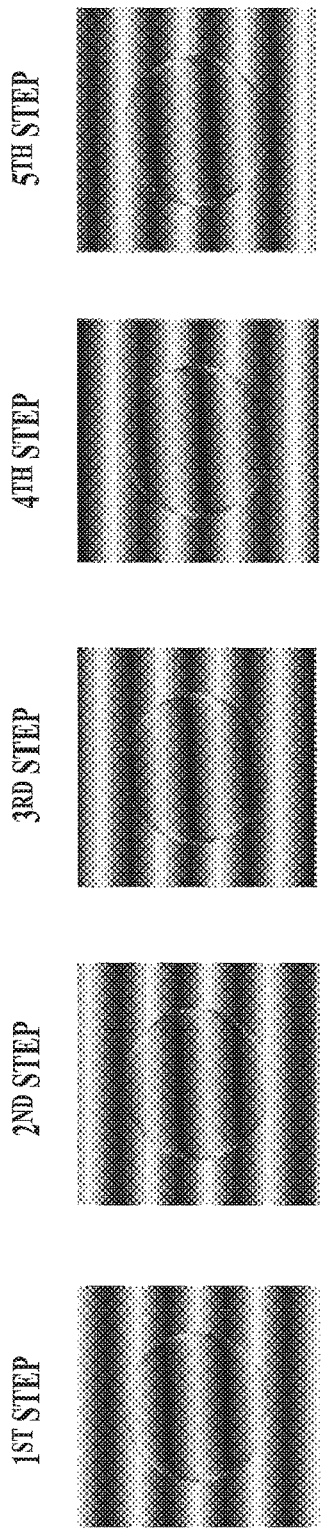
FIG. 7 shows moire images obtained by imaging of five steps.

Suppose, for example, the slit interval of the multi-slit 12 is 22.8 μm, and imaging of five steps takes ten seconds, each time the multi-slit 12 moves 4.56 μm, which is ⅕ of the slit interval, and stops, imaging is performed. In terms of imaging time, imaging is performed in two seconds, four seconds, six seconds, eight seconds and ten seconds after the exposure switch is turned on. If the multi-slit 12 is moved at a constant delivery amount thanks to ideal delivery accuracy, imaging of five steps produces five moire images for one interval of the slit interval of the multi-slit 12 as shown in FIG. 7.

When a series of imaging of steps finishes, the control unit 181 sends the moire images of the steps to the controller 5 through the communication unit 184 (Step S3). The communication unit 184 may send the obtained moire image to the controller 5 each time imaging of one step finishes, or may send all the obtained moire images thereto when imaging of all the steps finishes.

In the embodiment, a series of imaging with a subject placed on the subject table 13 and a series of BG imaging with no subject placed on the subject table 13 are performed, whereby subject moire images (subject-existing moire images) and BG moire images (no-subject-existing moire images) are obtained.

In the controller 5, when receives a series of subject moire images and a series of BG moire images from the main body unit 18 through the communication unit 54, the control unit 51 generates, based on the received series of subject moire images and series of BG moire images, reconstructed images, which are an absorption image, a differential phase image and a small-angle scattering image, and a differential absorption image (an image obtained by differentiating the absorption image), a differential small-angle scattering image (an image obtained by differentiating the small-angle scattering image) and a phase image (an image obtained by integrating the differential phase image), for example.

Signal values (pixel values) of a differential phase image, a differential absorption image and a differential small-angle scattering image, which are generated from a plurality of moire images, show different physical quantities. However, if the subject is bone(s), the signal values of the images have a certain correlation. If relative position of the radiation imaging device 1 and the subject changes while a plurality of moire images are being taken, because of the characteristics of reconstruction based on the principles of fringe scanning, error (change in signal value) occurs differently in the three images according to their moire phases and the change in relative position of the subject, which changes the relationship between the images. The inventor of this application has found out through a simulation and an experiment that image quality deterioration due to change in relative position of the radiation imaging device 1 and a subject can be detected by making use of change in relationship between the above images.

<Test with Simulation>

Figure 9A:
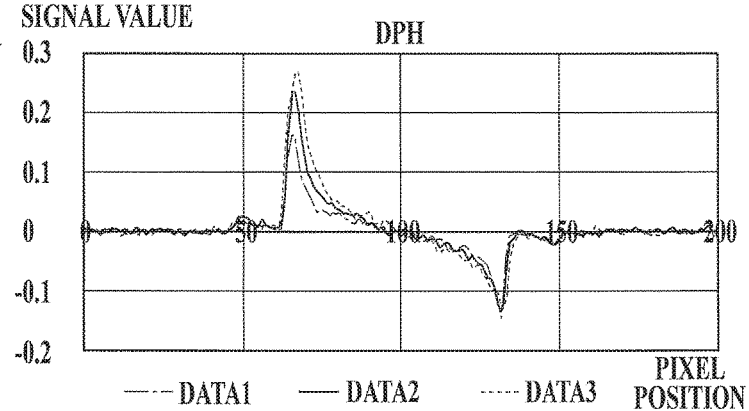
FIG. 9A shows profiles (at the center in the up-down direction) of differential phase images (DPH) of DATA1 to DATA3.
Figure 9B:
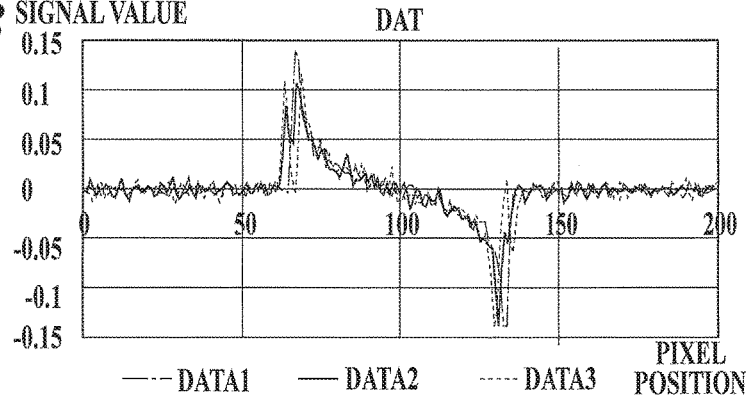
FIG. 9B shows profiles (at the center in the up-down direction) of differential absorption images (DAT) of DATA1 to DATA3.
Figure 9C:
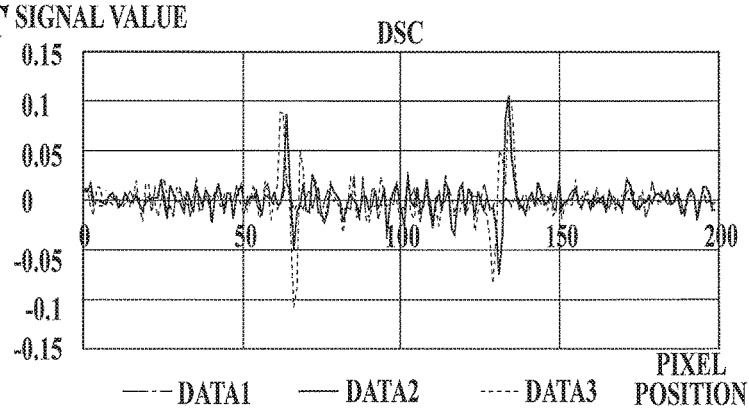
FIG. 9C shows profiles (at the center in the up-down direction) of differential small-angle scattering images (DSC) of DATA1 to DATA3.

FIG. 8 shows images generated by simulating a situation in which a subject does not move and a situation in which the subject moves. In the simulation, four moire images were generated by performing imaging four times while moving the multi-slit 12 ¼ of the slit interval for each imaging, and a differential phase image (DPH), an absorption image (AT) and a small-angle scattering image (SC) were generated based on the principles of fringe scanning, and also a differential absorption image (DAT) and a differential small-angle scattering image (DSC) were generated. In this simulation, calculation was performed on the assumption that moire fringes had been completely extended. The subject was an imitation of a human's joint formed of a bone sphere in a cartridge sphere surrounded with water. In FIG. 8, DATA1 shows images generated by simulating the situation in which the subject does not move, DATA2 shows images generated by simulating the situation in which the subject moves 50 µm for each imaging, i.e., 200 µm in total, in the upper right direction, and DATA3 shows images generated by simulating the situation in which the subject moves 100 µm for each imaging, i.e., 400 µm in total, in the upper right direction. In this simulation, calculation was performed by taking into account X-ray phase change and X-ray absorption change caused by the subject but not X-ray scatter caused by the subject, namely, by assuming that no scatter by the subject had occurred. FIG. 9A shows profiles (at the center in the up-down direction) of differential phase images (DPH) of DATA1 to DATA3. FIG. 9B shows profiles (at the center in the up-down direction) of differential absorption images (DAT) of DATA1 to DATA3. FIG. 9C shows profiles (at the center in the up-down direction) of differential small-angle scattering images (DSC) of DATA1 to DATA3. As it is understood from FIG. 8 and FIGS. 9A to 9C, when a subject moves, the signal values of a differential phase image (DPH), a differential absorption image (DAT) and a differential small-angle scattering image (DSC) change, but how error gets in (how the signal value changes) differs between these three images. This is characteristics of processing based on the principles of fringe scanning, and the error differs between the above three images according to their moire phases and/or the physical quantities, the moving direction and/or the moving amount of the subject.

FIGS. 10A to 12C are scatter diagrams created by plotting the signal values of the profiles shown in FIGS. 9A to 9C. The signal values of the water part were omitted from the scatter diagrams because they were 0 in all the three images.

Figure 10A:
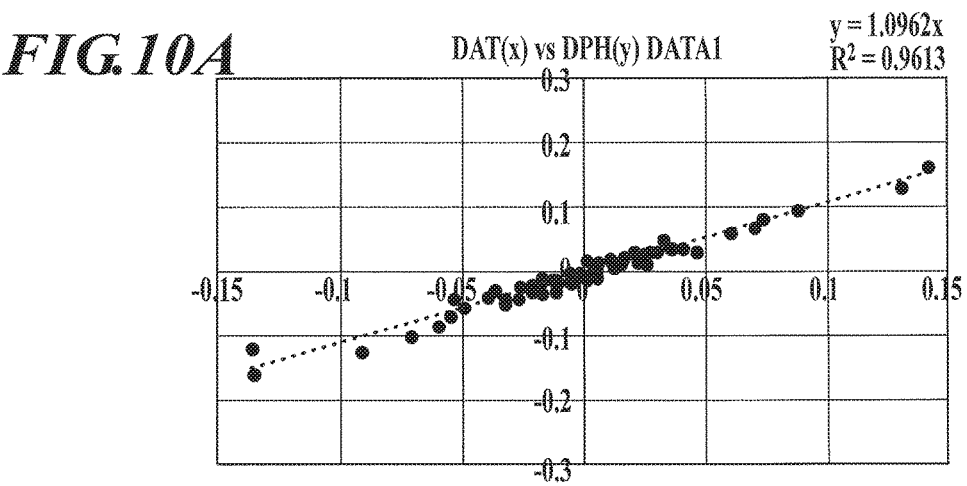
FIG. 10A is a scatter diagram of DATA1 of the differential absorption image and the differential phase image.
Figure 10B:
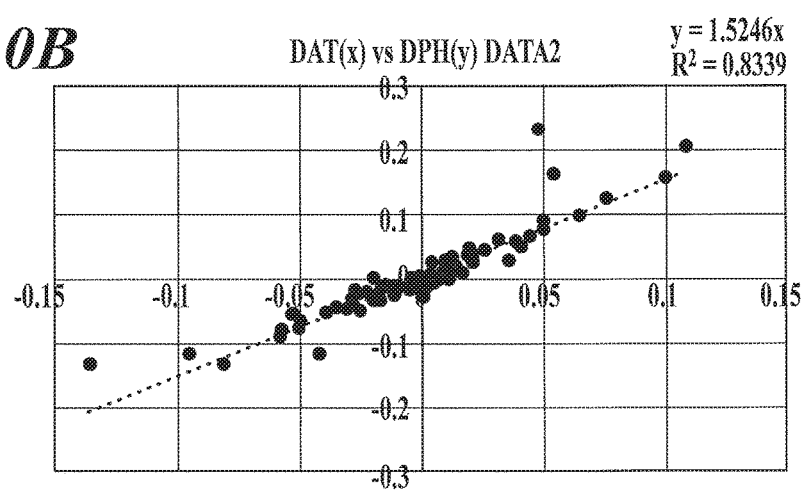
FIG. 10B is a scatter diagram of DATA2 of the differential absorption image and the differential phase image.
Figure 10C:
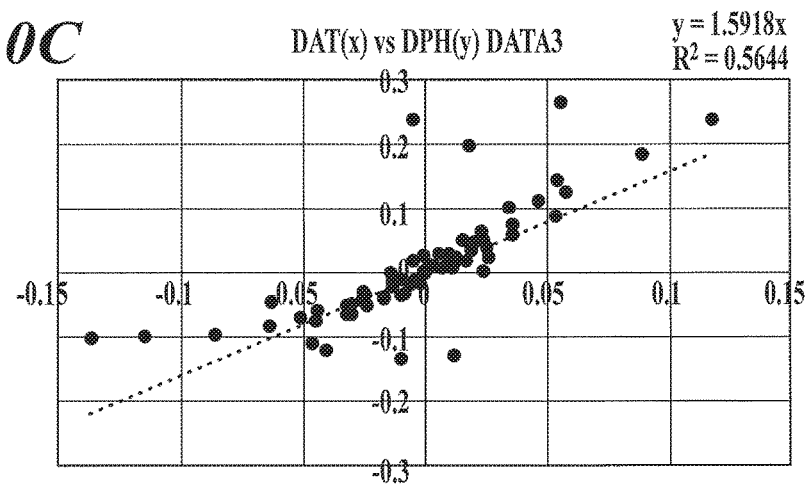
FIG. 10C is a scatter diagram of DATA3 of the differential absorption image and the differential phase image.
Figure 11A:
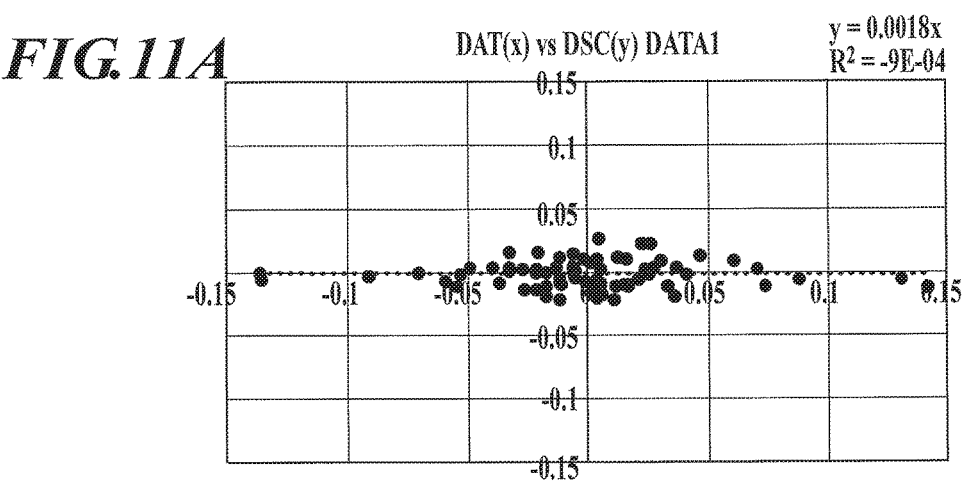
FIG. 11A is a scatter diagram of DATA1 of the differential absorption image and the differential small-angle scattering image.
Figure 11B:
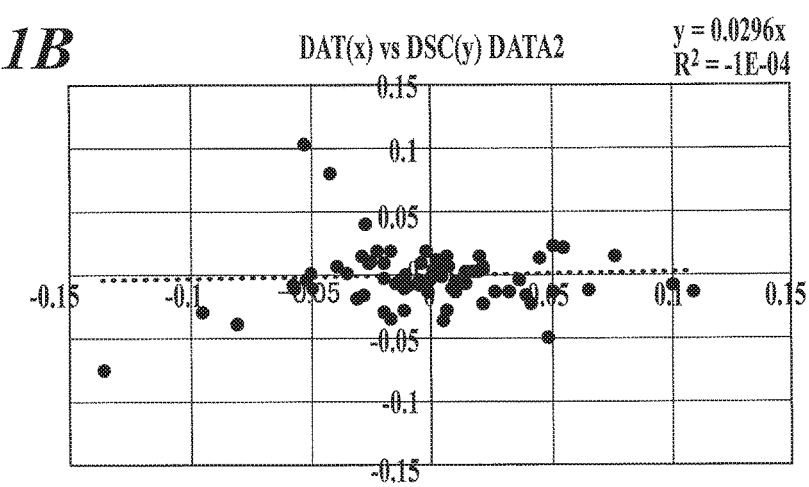
FIG. 11B is a scatter diagram of DATA2 of the differential absorption image and the differential small-angle scattering image.
Figure 11C:
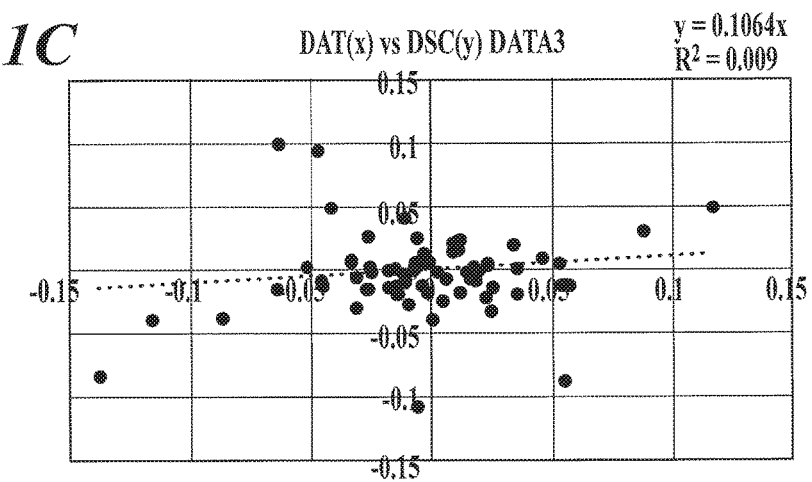
FIG. 11C is a scatter diagram of DATA3 of the differential absorption image and the differential small-angle scattering image.
Figure 12A:
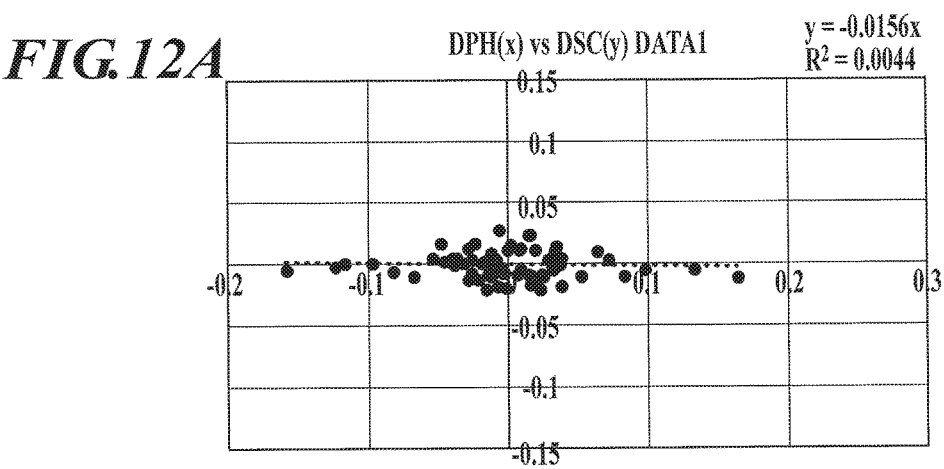
FIG. 12A is a scatter diagram of DATA1 of the differential phase image and the differential small-angle scattering image.
Figure 12B:
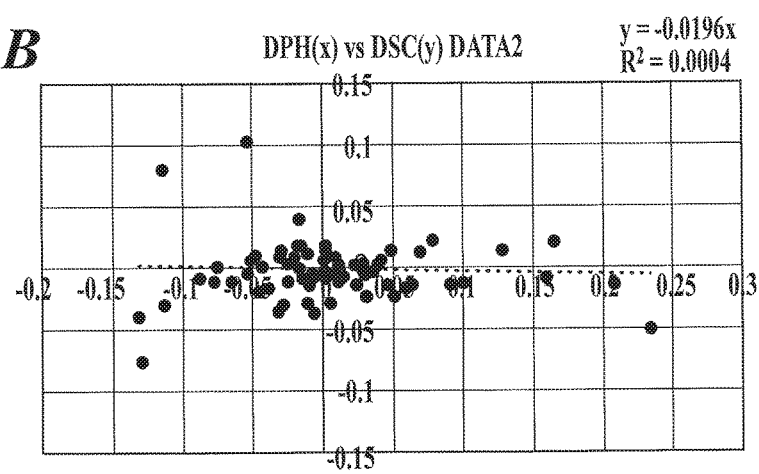
FIG. 12B is a scatter diagram of DATA2 of the differential phase image and the differential small-angle scattering image.
Figure 12C:
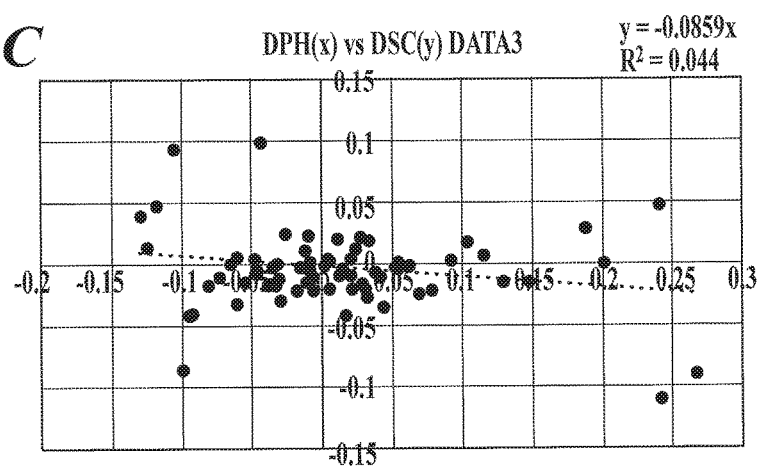
FIG. 12C is a scatter diagram of DATA3 of the differential phase image and the differential small-angle scattering image.

FIGS. 10A to 10C are respectively scatter diagrams of DATA1 to DATA3 of the differential absorption images and the differential phase images, in each of which x represents the signal value of the differential absorption image, and y represents the signal value of the differential phase image. FIGS. 11A to 11C are respectively scatter diagrams of DATA1 to DATA3 of the differential absorption images and the differential small-angle scattering images, in each of which x represents the signal value of the differential absorption image, and y represents the signal value of the differential small-angle scattering image. FIGS. 12A to 12C are respectively scatter diagrams of DATA1 to DATA3 of the differential phase images and the differential small-angle scattering images, in each of which x represents the signal value of the differential phase image, and y represents the signal value of the differential small-angle scattering image. Each scatter diagram is provided with a regression equation and a coefficient of determination R2 obtained by simple regression analysis on the values of x and y on the graph. The regression equation was obtained by the least squares method.

As it is understood from FIGS. 10A to 12C, in every image combination, the slope a1 of a regression line changes if a subject moves during fringe scanning, as compared with the case where the subject does not move during fringe scanning. This is because how error gets in differs between a differential phase image, a differential absorption image and a differential small-angle scattering image as described above. FIGS. 10A to 10C show a trend that the slope a1 becomes larger as a subject moves, but may become smaller as a subject moves, depending on the moire phase or how the subject moves. Image quality deterioration due to subject movement can be detected by: in advance, obtaining a slope (a reference a1) of a regression line (called "reference line") in a state in which a subject does not move, for each subject (for each imaging site or the like if the subject is a human body) and for each imaging condition (tube voltage, etc.), and storing the same in the storage unit 55; and comparing the slope (reference a1) of the reference line with the slope a1 of the regression line obtained from the image data (i.e., image data of a differential phase image, a differential absorption image and a differential small-angle scattering image generated based on moire images obtained by fringe scanning; the same applies hereinafter).

Because the scatter component by the subject was not taken into account in the simulation as described above, the slopes of the regression lines of DATA1 shown in FIGS. 11A and 12A, which includes the differential small-angle scattering image, are about 0. However, even if there is no X-ray scatter by a subject, when the subject moves, error occurs in a differential small-angle scattering image, and thereby the slope a1 changes. In FIGS. 11A to 12C, because the signal value of the differential small-angle scattering image is about 0, the coefficient of determination R2 is about 0 too. However, if signals of the differential small-angle scattering image are present, the coefficient of determination R2 changes. This is described below with experimental data.

As it is understood from the graphs, dispersion of the image data becomes large if a subject moves during fringe scanning, as compared with the case where the subject does not move during fringe scanning. The coefficient of determination R2 is an indicator which changes according to the slope. It cannot be generalized that when a subject moves, the coefficient of determination R2 decreases. However, image quality deterioration due to subject movement can be detected by: in advance, obtaining a coefficient of determination R2 (a reference R2) in a state in which a subject does not move, for each subject (for each imaging site or the like if the subject is a human body) and for each imaging condition (tube voltage, etc.), and storing the same in the storage unit 55; and comparing the reference R2 with the coefficient of determination R2 obtained from the image data. The coefficient of determination R2 tends to decrease according to subject movement on average. Hence, image quality deterioration due to subject movement may be roughly detected by making use of decrease in coefficient of determination R2. Other than the coefficient of determination R2, indictors indicating correlation, such as the coefficient of correlation R, may also be used.

The sum of errors (residuals) d (or a standard deviation σ) between (i) the image data and (ii) the regression line obtained from the image data or the reference line obtained in advance tends to increase according to subject movement. Hence, image quality deterioration due to subject movement can be detected based thereon.

In the simulation, for simplification, simple regression analysis, which uses a linear model, was used. Alternatively, high-order regression analysis, which uses a high-order model, may be used. For example, differential phase images are characterized in that signal(s) thereof appears lower than the actual one(s) against steep phase change of a subject, and hence use of high-order regression analysis has a possibility to detect subject movement more accurately. The model's order is preferably determined by taking into account required detection accuracy, model's stability, processing speed and so forth. The order may be changed according to the usage or subject.

Subject movement may be detected by multiple regression analysis with three images of a differential phase image, a differential absorption image and a differential small-angle scattering image, using a coefficient of multiple regression, errors from a multiple regression equation or a coefficient of determination.

<Test with Experimental Data>

Hereinafter, using experimental data, the result of a test on whether image quality deterioration due to subject movement can be detected based on an indicator value(s) of an indicator(s) indicating a relationship between images, the indicator value(s) being obtained by regression analysis, is described.

The subject used in the experiment was a hand phantom, which is an imitation of a human hand, and imaging was performed four times in fringe scanning. Because it was difficult to move the hand phantom while taking four moire images, four moire images were taken by fringe scanning without changing the position of the hand phantom, and thereafter the position of the hand phantom was slightly changed, and four moire images were taken by fringe scanning again. This was repeated, whereby four sets of moire images (16 moire images in total) different from one set to another in position of the hand phantom were taken. Subject movement was spuriously reproduced by combining these images.

FIG. 13 shows combinations of subject positions in generating moire images in the experiment. SET1 to SET4 are sets of experimental data each taken by fringe scanning. The subject positions are the same in a SET, but different from one SET to another. The moving amount of the subject is about 100 to 200 µm for each SET, and the moving direction is different from one SET to another. The pixel size is about 75 µm, and the enlargement ratio of the subject is about 1.3, so that the moving amount is about two pixels. Each of SET5 to SET8 is a combination of data of SET1 and data of SET2 and is a data set composed of four moire images one of which is slightly different from the other three in subject position. SET9 is a data set composed of four moire images respectively picked from SET1 to SET4, whereby the four moire images are different from one another in subject position. The moire images shown by shading in SET5 to SET9 in FIG. 13 correspond to data of the subject moved. Reconstruction was performed on each SET, whereby a differential phase image, an absorption image and a small-angle scattering image were generated with respect to each SET. In addition, differentiation was performed on the absorption image and the small-angle scattering image, whereby a differential absorption image and a differential small-angle scattering image were generated with respect to each SET.

Figure 14:
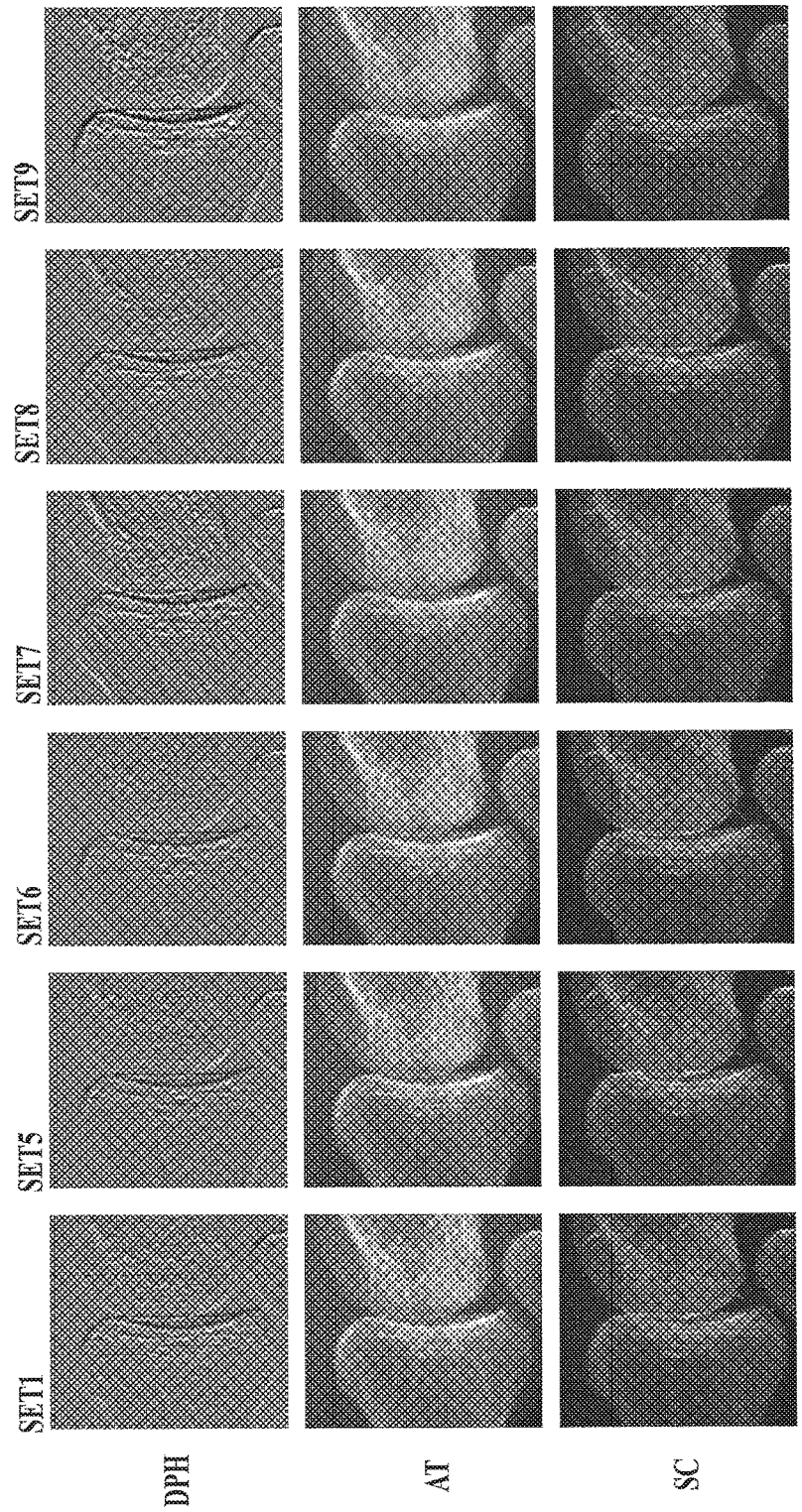
FIG. 14 shows differential phase images, absorption images and small-angle scattering images of SET1 and SET5 to SET9 in the experiment.

FIG. 14 shows the differential phase images (DPH), the absorption images (AT) and the small-angle scattering images (SC) of SET1 having no subject movement and SET5 to SET9 having subject movement. Display gradations of the differential phase images, the absorption images and the small-angle scattering images are −0.2π to 0.2π, 0.9 to 2.3, and 0.0 to 1.2, respectively.

As it is understood from FIG. 14, image change of SET5 to SET8, each of which was formed on the assumption that the subject slightly moved only one time, is small, so that it is difficult to judge influence of subject movement on the images by looking at SET1 and SET5 to SET8. When SET5 to SET8 are compared with SET1, difference therebetween may be determined. However, in actual imaging, an ideal right image(s) such as SET1 cannot be obtained because of mispositioning in subject position, subject angle or the like or individual difference (personal difference or temporal change if the subject is a human body). Therefore, difference between such images cannot be determined by looking at and comparing them.

SET5 to SET8 are each composed of four moire images one of which is different from the other three in subject position. Although the moire images different from the other moire images in subject position in SET5 to SET8 were obtained by moving the subject the same moving amount in the same moving direction, their influence on the differential phase images, the absorption images and the small-angle scattering images is different from one SET to another. This difference is originated from the grating position (moire phase) of the data replaced. For example, SET7 produced the differential phase image having signals stronger overall, the absorption image having signals slightly weaker, and the small-angle scattering image having signals slightly weaker and depiction of trabeculae lower than SET1, whereas SET8 produced the differential phase image having signals approximately the same, the absorption image having signals slightly weaker, and the small-angle scattering image having signals stronger and depiction of trabeculae higher (i.e., more clearly depicted) as/than SET1.

SET9 is composed of four moire images all different in subject position and was formed on the assumption that a human body was imaged. SET9 is approximately the same as each of SET5 to SET8 in the moving amount for each imaging, but the four moire images of SET9 are different from one another in the moving direction. Thereby, image quality deterioration and artifacts due to subject movement are relatively strongly shown therein. However, in actual imaging, in which an ideal right image(s) cannot be obtained, it is difficult for an operator to judge whether image quality deterioration and artifacts in an image(s) having subject movement, such as SET9, are due to movement of the subject or signal(s) of the subject itself. There is also a problem of variation in the judgment between operators, namely, a problem of personal equation.

(Detection by Simple Regression Analysis on One Image Combination Using Indicator)

Figure 15A:
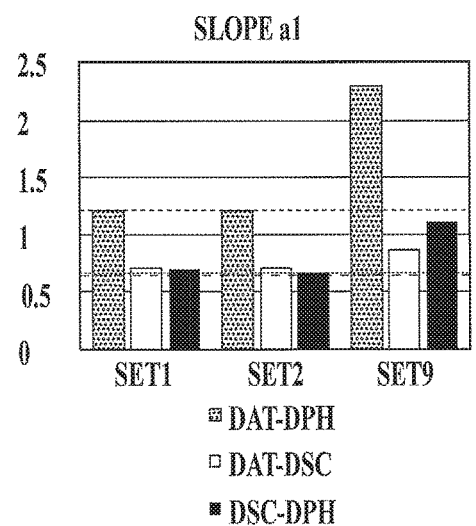
FIG. 15A is a graph of a slope a1 of a regression line.
Figure 15B:
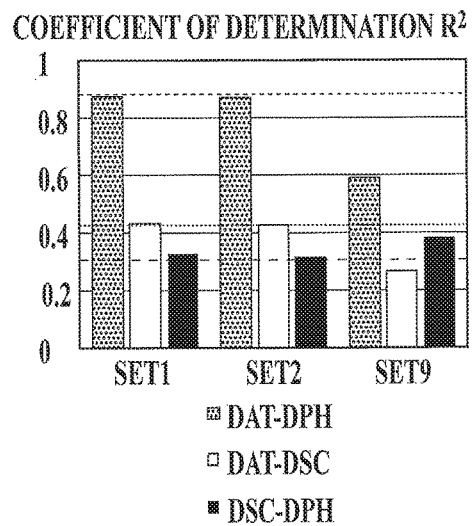
FIG. 15B is a graph of a coefficient of determination R2.
Figure 15C:
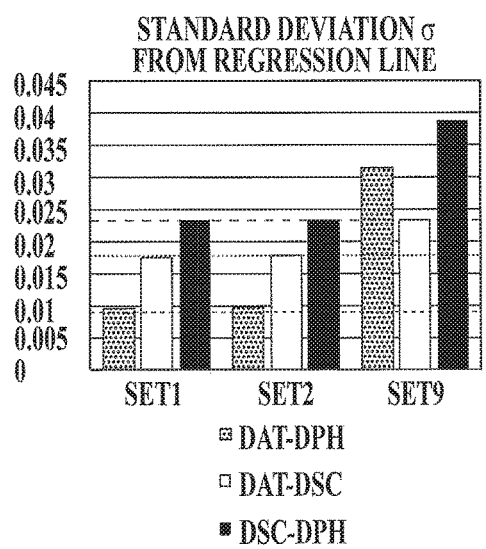
FIG. 15C is a graph of a standard deviation σ of the image data from the regression line.
Figure 15D:
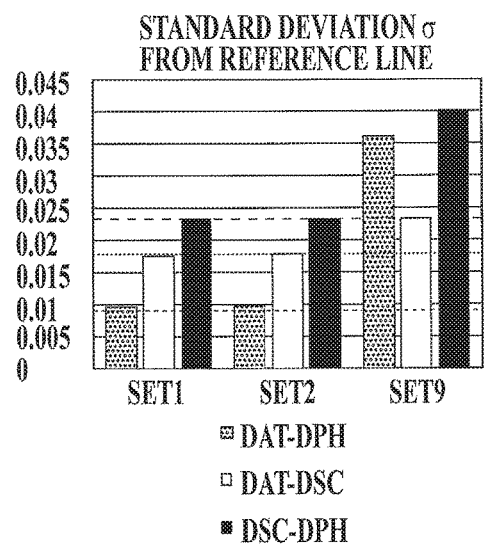
FIG. 15D is a graph of a standard deviation σ of the image data from a reference line.

FIGS. 15A to 15D show results of simple regression analysis with respect to each of SET1 and SET 2 having no subject movement and SET9 having subject movement, treating two images of the differential phase image (DPH), the differential absorption image (DAT) and the differential small-angle scattering image (DSC) as one image combination. FIG. 15A is a graph of the slope a1 of a regression line. FIG. 15B is a graph of the coefficient of determination R2 as a measure of goodness of fit of the regression line. FIG. 15C is a graph of the standard deviation 6 of the image data from the regression line. FIG. 15D is a graph of the standard deviation 6 of the image data from the reference line. The legends in the graphs show image combinations. DAT-DPH is a result of simple regression analysis with the differential absorption image as a dependent variable y and the differential phase image as an independent variable x, DAT-DSC is a result of simple regression analysis with the differential absorption image as a dependent variable y and the differential small-angle scattering image as an independent variable x, and DSC-DPH is a result of simple regression analysis with the differential small-angle scattering image as a dependent variable y and the differential phase image as an independent variable x. The dashed lines shown in the graphs in FIGS. 15A to 15D are values (reference values) obtained in advance in a state in which a subject did not move. In the experiment, they were obtained by averaging values of SET1 to SET4 having no subject movement. The dashed line with the shortest interval between dashes shows the reference value for DAT-DSC, the dashed line with the second shortest interval between dashes shows the reference value for DAT-DPH, and the dashed line with the longest interval between dashes shows the reference value for DSC-DPH.

In the experiment, as pre-processing for simple regression analysis, a binning process was performed on the differential phase image, the differential absorption image and the differential small-angle scattering image at 4×4 pixels, and then the bone part was extracted by making use of the small-angle scattering image. The extracted bone region was the target of simple regression analysis.

As shown in FIG. 15A, the values of the slope a1 of the regression line of the differential absorption image and the differential phase image (DAT-DPH), the slope a1 of the regression line of the differential small-angle scattering image and the differential phase image (DSC-DPH) and the slope a1 of the regression line of the differential absorption image and the differential small-angle scattering image (DAT-DSC) are almost the same as their respective reference values as to SET1 and SET2 having no subject movement, but 1.91 times, 1.23 times and 1.64 times larger than their respective reference values as to SET9 having subject movement. Thus, image quality deterioration due to subject movement can be detected by making use of that the slope a1 changes when a subject moves. More specifically, when the deviation quantity of the slope a1 of the regression line from its reference value, such as an absolute value of a difference between the slope a1 of the regression line and its reference value or a change rate obtained by dividing the slope a1 of the regression line by its reference value, is equal to or more than a threshold value, which is preset for each imaging site and for each imaging condition, it can be determined that image quality deterioration due to subject movement has been detected. The threshold value is preferably set not to detect the dispersion due to individual difference (difference between subjects), influence of positioning of a subject, X-ray emission conditions and so forth by mistaking it for the dispersion due to subject movement. Further, a plurality of threshold values may be set to provide a plurality of levels, such as a calling attention level and a warning level.

If the target of fringe scanning is a human body, because, as described above, bones show high correlation between a differential phase image and a differential absorption image and the relationship between the images is stable, it is preferable to use an image combination of a differential phase image and a differential absorption image to detect image quality deterioration due to bone movement. Further, a benefit of using the slope a1 as an indicator to detect image quality deterioration due to subject movement is that, as compared with the below-described coefficient of determination R2 and errors d (lengths of line segments drawn from image data points to a regression line along the y axis), the slope a1 is little affected by image graininess and enables relatively stable detection of image quality deterioration due to subject movement, regardless of the X-ray dose or the subject thickness in the X-ray emission direction. In addition, the coefficient of determination R2 and the errors d need different reference values according to the X-ray dose or the subject thickness, but the slope a1 does not need them and hence the number of reference values for the slope a1 can be a small number.

As shown in FIG. 15B, the values of the coefficient of determination R2 of the differential absorption image and the differential phase image (DAT-DPH), the coefficient of determination R2 of the differential small-angle scattering image and the differential phase image (DSC-DPH) and the coefficient of determination R2 of the differential absorption image and the differential small-angle scattering image (DAT-DSC) are almost the same as their respective reference values as to SET1 and SET2 having no subject movement, but 0.66 times, 0.62 times and 1.19 times larger than their respective reference values as to SET9 having subject movement. Thus, image quality deterioration due to subject movement can be detected by making use of that the coefficient of determination R2 changes when a subject moves. More specifically, when the deviation quantity of the coefficient of determination R2 from its reference value, such as an absolute value of a difference between the coefficient of determination R2 and its reference value or a change rate obtained by dividing the coefficient of determination R2 by its reference value, is equal to or more than a threshold value, which is preset for each imaging site and for each imaging condition, it can be determined that image quality deterioration due to subject movement has been detected. The threshold value is preferably set not to detect the dispersion due to individual difference, influence of positioning of a subject, X-ray emission conditions and so forth by mistaking it for the dispersion due to subject movement. Further, a plurality of threshold values may be set to provide a plurality of levels, such as a calling attention level and a warning level.

As shown in FIG. 15C, the values of the standard deviation $\sigma$ of the image data from the regression line about the differential absorption image and the differential phase image (DAT-DPH), the standard deviation 6 of the image data from the regression line about the differential small-angle scattering image and the differential phase image (DSC-DPH) and the standard deviation $\sigma$ of the image data from the regression line about the differential absorption image and the differential small-angle scattering image (DAT-DSC) are almost the same as their respective reference values as to SET1 and SET2 having no subject movement, but are 3.27 times, 1.3 times and 1.65 times larger than their respective reference values as to SET9 having subject movement. Similarly, as shown in FIG. 15D, the values of the standard deviations $\sigma$ of the image data from the reference lines about the respective image combinations are almost the same as their respective reference values as to SET1 and SET2 having no subject movement, but depart from their respective reference values as to SET9 having subject movement. Thus, image quality deterioration due to subject movement can be detected by making use of that the standard deviation $\sigma$ changes when a subject moves. More specifically, when the deviation quantity of the standard deviation $\sigma$ from its reference value, such as an absolute value of a difference between the standard deviation $\sigma$ and its reference value or a change rate obtained by dividing the standard deviation $\sigma$ by its reference value, is equal to or more than a threshold value, which is preset for each imaging site and for each imaging condition, it can be determined that image quality deterioration due to subject movement has been detected. The threshold value is preferably set not to detect the dispersion due to individual difference, influence of positioning of a subject, X-ray emission conditions and so forth by mistaking it for the dispersion due to subject movement. Further, a plurality of threshold values may be set to provide a plurality of levels, such as a calling attention level and a warning level.

Examples of the indicator to detect image quality deterioration due to subject movement are not limited to: the slope a1 of a regression line; the coefficient of determination R2; the standard deviation $\sigma$ from the regression line; and the standard deviation $\sigma$ from the reference line (regression equation), which are described above, but include: the coefficient of correlation R; and general indicators of error, such as the arithmetic mean of absolute values of errors d between the regression line and the image data, and the arithmetic mean of absolute values of errors d between the reference line and the image data.

When dispersion of the image data such as the standard deviation $\sigma$ is used as the indicator, a difference thereof from its reference value can be used as described above. However, image quality deterioration due to subject movement may be detected simply according to the magnitude of the indicator value, by making use of the trend that dispersion of the image data becomes large when a subject moves. As with the coefficient of determination R2 and so forth, in some cases, the indicator of one image combination cannot accurately detect image quality deterioration due to subject movement, but can detect the image quality deterioration when a subject relatively largely moves (SET9).

(Detection by Simple Regression Analysis on Plurality of Image Combinations Using Indicator)

FIGS. 16A to 16D show results of simple regression analysis with respect to each of SET1 and SET 2 having no subject movement and SET5 to SET9 having subject movement, treating two of the differential phase image (DPH), the differential absorption image (DAT) and the differential small-angle scattering image (DSC) as one image combination, wherein indicator values of a plurality of image combinations are combined. FIG. 16A is a graph of the root mean square (rms) of differences between the slopes a1 of the regression lines and the references a1. FIG. 16B is a graph of the root mean square of differences between the coefficients of determination R2 and the references R2. FIG. 16C is a graph of the root mean square of the standard deviations $\sigma$ of the image data from the regression lines. FIG. 16D is a graph of the root mean square of the standard deviations $\sigma$ of the image data from the reference lines.

As shown in FIGS. 16A and 16B, when change in slope a1 and change in coefficient of determination R2 are used as the indicator, there is a large difference even between (i) SET1 and SET2 having no subject movement and (ii) SET5 to SET8 having slight subject movement. That is, image quality deterioration due to subject movement can be detected by making use of the root mean square of the differences between the slopes a1 of the regression lines and the references a1 or the root mean square of the differences between the coefficients of determination R2 and the references R2. More specifically, when the root mean square of the differences between the slopes a1 of the regression lines and the references a1 or the root mean square of the differences between the coefficients of determination R2 and the references R2 is equal to or more than a threshold value, which is preset for each imaging site and for each imaging condition, it can be determined that image quality deterioration due to subject movement has been detected.

As shown in FIGS. 16C and 16D, as to both the root mean square of the standard deviations 6 of the image data from the regression lines and the root mean square of the standard deviations 6 of the image data from the reference lines, the values of SET5 to SET8 having slight subject movement are almost the same as those of SET1 and SET2 having no subject movement. Hence, it is difficult to detect image quality deterioration due to subject movement based thereon. However, image quality deterioration due to subject movement can be detected based thereon when a subject relatively largely moves, such as SET9, by setting their threshold values at moderate values.

Examples of the indicator to detect image quality deterioration due to subject movement are not limited to those shown in FIGS. 16A to 16D but include: the root mean square of the slopes a1 of the regression lines; the root mean square of the coefficients of determination R2; the root mean square of the coefficients of correlation R; the root mean square of the arithmetic means of the absolute values of the errors (residuals) d between the regression lines and the image data; the root mean square of the arithmetic means of the absolute values of the errors d between the reference lines and the image data; and the root mean square of differences between the above and their reference values.

Whether a subject moves or not may be determined as a whole by combining a plurality of indicators. For example, the condition to determine that image quality deterioration due to subject movement has been detected may be as follows; when the slope(s) a1 is equal to or more than a predetermined threshold value(s) and also the standard deviation(s) σ is equal to or more than a predetermined threshold value(s). Indicators may be normalized and the average or the root mean square thereof may be used. Alternatively, indicators may each be weighted and the average or the root mean square thereof may be used.

(Detection by Multiple Regression Analysis Using Indicator)

Figure 17A:
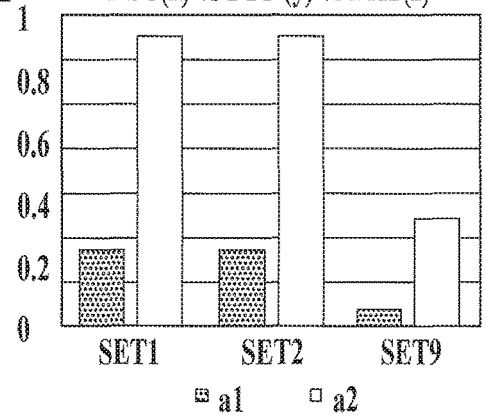
FIG. 17A is a graph of a coefficient of regression a1 and a coefficient of regression a2 obtained by multiple regression analysis.
Figure 17B:
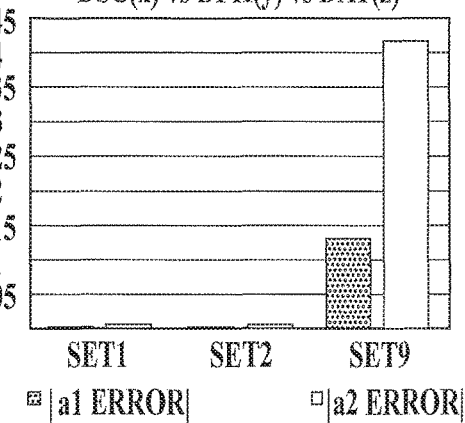
FIG. 17B is a graph of an a1 error and an a2 error.
Figure 17C:
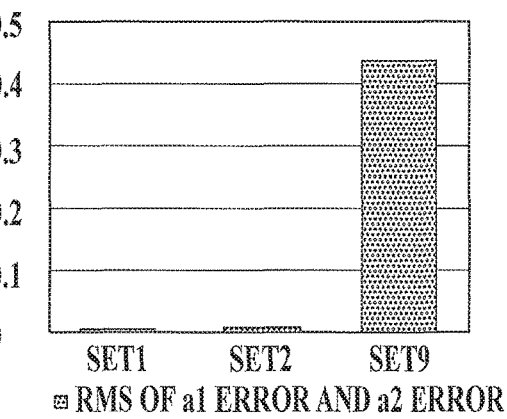
FIG. 17C is a graph of the root mean square of the a1 error and the a2 error.

FIGS. 17A to 17C show results of multiple regression analysis with respect to each of SET1 and SET2 having no subject movement and SET9 having subject movement, treating the differential small-angle scattering image (DSC) and the differential phase image (DPH) as dependent variables and the differential absorption image (DAT) as an independent variable. FIG. 17A is a graph of coefficients of regression a1 and a2. FIG. 17B is a graph of differences between the coefficients of regression a1 and a2 and their respective reference values obtained in advance in a state in which a subject did not move (the differences are respectively called "a1 error" and "a2 error"). FIG. 17C is a graph of the root mean square of the a1 error and the a2 error (FIG. 17C).

As shown in FIGS. 17A to 17C, as to all the coefficients of regression a1 and a2, the a1 and a2 errors, and the root mean square of the a1 error and the a2 error, the values of SET1 and SET2 having no subject movement are greatly different from those of SET9 having subject movement. Hence, image quality deterioration due to subject movement can be detected by multiple regression, as with simple regression.

In the above, the method for detecting image quality deterioration due to subject movement is described with the simulation and experimental data. However, the radiation imaging device 1 moving in relation to a subject and the subject moving in relation to the radiation imaging device 1 bring the same effect (situation), and therefore when the radiation imaging device 1 moves by vibrations or the like, image quality deterioration occurs too. That is, image quality deterioration due to movement of the radiation imaging device 1 in relation to a subject can be detected by the same method as the above. In non-destructive usages, there is no situation that the target, such as an aluminum casting or an electronic component, moves, but it is expected that the radiation imaging device 1 moves and thereby image quality deterioration occurs.

<Action of Controller 5>

Hereinafter, an action of the controller 5 is described.

The controller 5 performs a reconstructed image generation process, thereby generating reconstructed images based on moire images sent from the radiation imaging device 1, and also determines based on an indicator value(s) indicating a relationship between the reconstructed images or the like, the indicator value being obtained by the above-described regression analysis, whether image quality deterioration due to change in relative position of the radiation imaging device 1 and a subject occurs in the reconstructed images.

FIG. 18 is a flowchart of the reconstructed image generation process performed by the control unit 51 of the controller 5. The reconstructed image generation process is performed by the controller 51 in cooperation with the program(s) stored in the storage unit 55.

First, the control unit 51 stores in the RAM a series of moire images received from the main body unit 18 of the radiation imaging device 1 through the communication unit 54, and generates reconstructed images based on the received series of moire images (Step S11).

More specifically, the control unit 51 generates three types of reconstructed images, an absorption image, a differential phase image and a small-angle scattering image, based on M subject moire images and M BG moire images.

The above three types of reconstructed images can be generated by a well-known method described, for example, in International Patent Application Publication No. 2012/029340.

First, the control unit 51 performs, for example, offset correction, gain correction, defective pixel correction and/or X-ray intensity variation correction on the subject moire images and the BG moire images. Next, the control unit 51 generates three types of subject-existing reconstructed images (absorption image, differential phase image and small-angle scattering image) based on the corrected subject moire images. In addition, the control unit 51 generates three types of no-subject-existing reconstructed images (absorption image, differential phase image and small-angle scattering image) based on the corrected BG moire images.

More specifically, the control unit 51 generates each absorption image by adding up moire fringes of M moire images, generates each differential phase image by calculating the moire phase using the principles of fringe scanning, and generates each small-angle scattering image by calculating the moire visibility (visibility=amplitude/average value) using the principles of fringe scanning.

Next, the control unit 51 performs correction processes to remove the moire phase and to remove image unevenness (artifacts) from each subject-existing reconstructed image, using its corresponding no-subject-existing reconstructed image, thereby generating the reconstructed images of the final version.

For example, with respect to the subject-existing reconstructed image being the differential phase image, the control unit 51 subtracts, from the signal value of each pixel of the subject-existing differential phase image, the signal value of its corresponding pixel (pixel at the same position) of the no-subject-existing differential phase image (Reference Document 4; Timm Weitkamp, Ana Diazand, Christian David, Franz Pfeiffer and Marco Stampanoni, Peter Cloetens and Eric Ziegler, X-ray Phase Imaging with a grating interferometer, OPTICSEXPRESS, Vol. 13, No. 16, 6296-6004 (2005), and Reference Document 5; Atsushi Momose, Wataru Yashiro, Yoshihiro Takeda, Yoshio Suzuki and Tadashi Hattori, Phase Tomography by X-ray Talbot Interferometry for Biological Imaging, Japanese Journal of Applied Physics, Vol.45, No. 6A, 2006, pp. 5254-5262 (2006)).

With respect to the subject-existing reconstructed image being the absorption image or the small-angle scattering image, the control unit 51 divides the signal value of each pixel of the subject-existing reconstructed image by the signal value of its corresponding pixel of the no-subject-existing reconstructed image (Reference Document 6; F.

Pfeiffer, M. Bech, O. Bunk, P. Kraft, E. F. Eikenberry, CH. Broennimann, C. Grunzweig, and C. David, Hard-X-ray dark-field imaging using a grating interferometer, nature materials Vol. 7, 134-137 (2008)).

Next, the control unit 51 differentiates the absorption image generated at Step S11, thereby generating a differential absorption image, and also differentiates the small-angle scattering image generated at Step S11, thereby generating a differential small-angle scattering image (Step S12).

Next, the control unit 51 pre-processes the differential phase image, the differential absorption image and the differential small-angle scattering image before regression analysis (Step S13).

At Step S13, the control unit 51 performs, as the pre-processing, extraction of pixels which are the target of regression analysis and the binning process or the like.

In the reconstructed image generation process, change in relationship between a differential phase image, a differential absorption image and a differential small-angle scattering image is used to detect image quality deterioration due to change in relative position of the radiation imaging device 1 and a subject occurring in a reconstructed image(s). However, if the subject is constituted of a plurality of materials, the relationship between the images is different from one material to another. Hence, correlation of the images decreases and change in relationship between the images becomes random, which disables detection of image quality deterioration due to change in relative position of the radiation imaging device 1 and the subject or makes the detection unstable. Therefore, preferably, regression analysis uses only pixel data having the same composition.

For example, if the subject is a human body, which has complex composition (tissue), preferably, pixels depicting bones or skin are extracted as the target of regression analysis. Bones and skin surface each show contrast in all the differential phase image, differential absorption image and differential small-angle scattering image, and these three images have a certain relationship. Trabeculae of bones or winkles of skin greatly change signals of the images, and hence change in relationship between the images can be easily detected.

For extraction of bones, signals of a small-angle scattering image can be preferably used. In a small-angle scattering image, bones produce strong signals whereas soft parts do not provide contrast. Hence, only bones can be extracted stably from the image, regardless of the thickness of the soft parts. For extraction of skin, signals of a differential phase image or a small-angle scattering image can be preferably used. In a differential phase image or a small-angle scattering image, the boundary between skin and air provides very strong contrast. Hence, skin can be easily extracted from either of the images by making use of that the signals around skin are flat because they depict air. In the case of non-destructive examinations too, preferably, regression analysis uses only data having the same composition.

Before or after selection of the pixels which are the target of regression analysis, preferably, the binning process or a filtering process is performed on the differential phase image, the differential absorption image and the differential small-angle scattering image. The binning process can reduce the dispersion due to photon noise and can increase stability of detection of image quality deterioration due to subject movement against the X-ray dose or the subject thickness. A benefit of using the binning process is reduction of the calculation amount. The filtering process can exhibit the same effect as the binning process by blurring the images with a frequency filter or a spatial filter.

If a region having strong noise is used as the target of regression analysis, the relationship between the images is dominantly random, and thereby image quality deterioration due to change in relative position of the radiation imaging device 1 and a subject cannot be accurately detected. Hence, it is preferable to, in the pre-processing, extract pixels having strong noise (noise pixels) and exclude the extracted noise pixels from the target of regression analysis. The method for extracting noise pixels is not particularly limited, and is exemplified by a method of obtaining a phase error $\sigma\Phi(x,y)$ of each pixel of BD moire images and extracting pixels each having a value of the phase error $\sigma\Phi(x,y)$ larger than a predetermined threshold value as noise pixels.

The phase error $\sigma\Phi(x,y)$ can be defined by the following formulae.

$$\sigma\Phi(x, y) = \frac{1}{\sqrt{2M}\,\pi} \sqrt{\frac{\alpha}{a_0(x, y) vis(x, y)^2}} \quad \text{[Formula 1]}$$

$$a_0(x, y) = \frac{\sum_{k=0}^{M-1} I_k(x, y)}{M} \quad \text{[Formula 2]}$$

$$vis(x, y) = \frac{a_1(x, y)}{a_0(x, y)} = \frac{2\left|\sum_{k=0}^{M-1} I_k(x, y)\exp\left(-2\pi i \frac{k}{M}\right)\right|}{\sum_{k=1}^{M} I_k(x, y)} \quad \text{[Formula 3]}$$

In the above formulae, I represents an X-ray intensity signal value, x and y represent two-dimensional coordinates of moire images, M represents how many times imaging is performed in fringe scanning, a represents a coefficient related to sensitivity of the radiation detector 16 (hereinafter called a coefficient of sensitivity) to convert X-ray photons into detector signals. The coefficient of sensitivity depends on X-ray energy.

Because subject moire images and BD moire images cannot be taken at the same time, they are taken separately. If imaging conditions (arrangements of gratings, etc.) change between fringe scanning for subject moire images and fringe scanning for BD moire images, artifacts appear in a differential phase image. Then, the relationship between the differential phase image and the other images contains statistical error, and thereby image quality deterioration due to change in relative position of the radiation imaging device 1 and a subject may be not accurately detected. Hence, it is preferable to, before regression analysis, perform a process to correct artifacts generated by change in imaging conditions. Examples of the correction process to correct artifacts generated by change in imaging conditions include correction with a linear function and correction with a quadratic function which are described, for example, in Japanese Patent Application Publication No. 2012-170618. In the case where a curved grating(s) is used to reduce influence of angle of incident of X-rays, change in curvature is concerned. Then, the correction process may be correction with a high-order function, such as a cubic function or a higher-order function.

When finishes the pre-processing, the control unit 51 performs a detection process of image quality deterioration due to change in relative position of the radiation imaging device 1 and the subject (Step S14).

At Step S14, as described above, the control unit 51 performs simple regression analysis, treating two images of the differential phase image, the differential absorption image and the differential small-angle scattering image as one image combination, and calculates an indicator value of an indicator indicating a relationship between the two images. Examples of the indicator include a slope a1 of a regression line, a coefficient of determination R2, a standard deviation σ of data from the regression line and a standard deviation σ of data from a reference line. The control unit 51 then detects image quality deterioration due to change in relative position of the radiation imaging device 1 and the subject based on the calculated indicator value. More specifically, the control unit 51 determines that image quality deterioration due to change in relative position of the radiation imaging device 1 and the subject has been detected when an absolute value of a difference between the calculated indicator value and its predetermined reference value stored in the storage unit 55 or a change rate obtained by dividing the calculated indicator value by the reference value is equal to or more than a predetermined threshold value.

Alternatively, as described above, the control unit 51 may perform simple regression analysis, treating two images of the differential phase image, the differential absorption image and the differential small-angle scattering image as one image combination, and determine that image quality deterioration due to change in relative position of the radiation imaging device 1 and the subject has been detected when an indicator value of an indicator composed of indicator values (e.g., the root mean square of indicator values) of a plurality of image combinations is equal to or more than a predetermined threshold, or when an absolute value of a difference between the calculated indicator value and its predetermined reference value or a change rate obtained by dividing the calculated indicator value by the reference value is equal to or more than a predetermined value.

Alternatively, as described above, the control unit 51 may perform multiple regression analysis, treating three images of the differential phase image, the differential absorption image and the differential small-angle scattering image as one image combination, and calculate an indicator value of an indicator indicating a relationship between the three images. Examples of the indicator include a coefficient of multiple regression, errors from a multiple regression equation and a coefficient of determination. The control unit 51 then detects image quality deterioration due to change in relative position of the radiation imaging device 1 and the subject based on the calculated indicator value, as with the case of simple regression analysis.

When detects (determines) image quality deterioration due to change in relative position of the radiation imaging device 1 and the subject as a result of the detection process (Step S15; YES), the control unit 51 displays on the display unit 53 the reconstructed images and a message to warn (warning message) that image quality deterioration due to change in relative position of the radiation imaging device 1 and the subject occurs (Step S16) and moves to Step S18.

On the other hand, when detects (determines) no image quality deterioration due to change in relative position of the radiation imaging device 1 and the subject as a result of the detection process (Step S15; NO), the control unit 51 displays the reconstructed images on the display unit 53 (Step S17) and moves to Step S18.

On the display unit 53, together with the warning message and/or the reconstructed images, a storage button to store reconstructed images and a delete button to delete reconstructed images without storing are displayed.

Thus, displaying a message to warn that image quality deterioration due to change in relative position of the radiation imaging device 1 and a subject occurs in reconstructed images together with the reconstructed images when detecting such image quality deterioration lets an operator such as a radiologist recognize that image quality deterioration occurs and its cause is change in relative position of the radiation imaging device 1 and a subject. Consequently, the operator can appropriately handle the situation, for example, by asking the patient or the like not to move the subject or fixing the subject and then re-imaging the subject. Further, when no warning message is displayed but image quality deterioration is recognized with eyes, the operator can understand that its cause is other than change in relative position of the radiation imaging device 1 and the subject. Consequently, the operator can appropriately handle the situation, for example, by re-positioning the subject (in position and/or angle) and then re-imaging the subject.

At Step S18, the control unit 51 determines whether to receive, from the operation unit 52, a command to store the reconstructed images or a command to delete the reconstructed images.

When receives, from the operation unit 52, the command to store the reconstructed images (Step S18; YES), the control unit 51 correlates and stores in the storage unit 55 the reconstructed images and the moire images, based on which the reconstructed images have been generated, with patient information (Step S19) and ends the reconstructed image generation process.

On the other hand, when receives, from the operation unit 52, the command to delete the reconstructed images (Step S18; NO), the control unit 51 deletes the reconstructed images and the moire images, based on which the reconstructed images have been generated, from the RAM (Step S20) and ends the reconstructed image generation process.

As described above, the control unit 51 of the controller 5 performs regression analysis on signal values (image data) of at least two images of a differential phase image, a differential absorption image and a differential small-angle scattering image, calculates an indicator value of an indicator indicating a relationship between the images, and detects image quality deterioration due to change in relative position of the radiation imaging device 1 and the subject based on the calculated indicator value.

For example, the control unit 51 performs simple regression analysis on at least one image combination, treating two images of a differential phase image, a differential absorption and a differential small-angle scattering image as one image combination, and calculates an indicator value of an indicator indicating a relationship between the images. Examples of the indicator include a coefficient of regression, a coefficient of determination, a standard deviation from a regression equation, a coefficient of correlation, and an error(s) from the regression equation. The control unit 51 then detects image quality deterioration due to change in relative position of the radiation imaging device 1 and the subject based on a difference between the calculated indicator value and an indicator value (reference value) of the indicator obtained in advance from image data having no change in relative position of the radiation imaging device 1 and the subject or based on a change rate obtained by dividing the calculated indicator value by the reference value.

Consequently, image quality deterioration due to change in relative position of the radiation imaging device 1 and a subject can be detected from image data without using a special tool such as a marker.

Further, if the subject is a human body, the control unit 51 extracts a pixel(s) of a bone part from the images, which are the target of the regression analysis, and performs the regression analysis, using only data of the extracted pixel(s) of the bone part so as to detect image quality deterioration due to change in relative position of the radiation imaging device 1 and the subject. This enables stable detection thereof.

Further, the control unit 51 performs, before the regression analysis, a binning process or a filtering process, described above, on the images, which are the target of the regression analysis. This can reduce the dispersion due to photon noise and can increase stability of detection of image quality deterioration due to subject movement against the radiation dose or the subject thickness.

Further, the control unit 51 extracts a noise pixel(s) from the images, which are the target of the regression analysis, and (ii) excludes the extracted noise pixel(s) from the target of the regression analysis. This enables detection of subject movement with high accuracy.

Further, the control unit 51 controls the display unit 53 to display a warning when detects image quality deterioration due to change in relative position of the radiation imaging device 1 and the subject. This lets an operator recognize that image quality deterioration occurs in the generated reconstructed images and its cause is change in relative position of the radiation imaging device 1 and the subject. Consequently, the operator can appropriately handle the situation, for example, by asking the patient or the like not to move the subject or fixing the subject and then re-imaging the subject.

The description in the above embodiment is merely one preferred example of the present invention, and hence the present invention is not limited thereto.

For example, in the above embodiment, the radiation imaging device 1 uses a Talbot-Lau interferometer employing the method of moving the multi-slit 12 in relation to the first grating 14 and the second grating 15 in fringe scanning. However, the present invention is also applicable to a radiation imaging device which uses a Talbot-Lau interferometer employing a method of moving one or two of the multi-slit 12, the first grating 14 and the second grating 15 in relation to the other(s). The present invention is also applicable to a radiation imaging device which uses a Talbot interferometer employing a method of moving one of the first grating 14 and the second grating 15 in relation to the other.

Further, in the above embodiment, the radiation imaging system includes the multi-slit 12, the first grating 14 and the second grating 15, which are one-dimensional gratings. However, the present invention is also applicable to a radiation imaging system which includes two-dimensional gratings and performs fringe scanning two-dimensionally.

Further, in the above embodiment, image quality deterioration due to change in relative position of the radiation imaging device 1 and a subject is detected by making use of change in relationship between a differential phase image, a differential absorption image and/or a differential small-angle scattering image. However, a phase image (PH) obtained by integrating a differential phase image, an absorption image (AT) and a small-angle scattering image (SC) have a certain relationship too, and therefore, when image quality deterioration due to change in relative position of the radiation imaging device 1 and a subject occurs, the relationship between these images also changes according to the subject movement and their moire phases, as with the relationship between the above differential images (i.e., a differential phase image, a differential absorption image and a differential small-angle scattering image). Hence, image quality deterioration due to change in relative position of the radiation imaging device 1 and a subject may be detected by making use of change in relationship between at least two (three in the case of multiple regression analysis) of a phase image, an absorption image and a small-angle scattering image, instead of differential images.

Further, in images obtained by imaging with a radiation imaging device composed of a plurality of line detectors combined with a plurality of line gratings as described in Japanese Patent Application Publication (Translation of PCT Application) No. 2009-543080 too, image quality deterioration due to change in relative position of the radiation imaging device and a subject can be detected by the method described in the above embodiment. This device is configured to perform scanning by moving a subject or the radiation imaging device, and hence it is expected to move a device which carries a subject or to move the radiation imaging device when the radiation imaging device performs scanning. In the case of this device, moire data successively obtained by the line detectors are one-dimensional data, but two-dimensional worth data can be obtained by connecting these one-dimensional data with one another. Image quality deterioration due to change in relative position of the radiation imaging device and a subject may be detected by regression analysis on (i) one-dimensional data of a differential phase image, a differential absorption image and a differential small-angle scattering image obtained from the one-dimensional moire data or (ii) a differential phase image, a differential absorption image and a differential small-angle scattering image obtained from moire images composed of the two-dimensional worth data. However, if a shift in the carrying direction or the scanning direction of the radiation imaging device occurs line by line due to error in timing of obtaining one-dimensional moire data, change in speed in the carrying direction or the scanning direction of the radiation imaging device, or the like, it is preferable to process the former, namely, perform regression analysis on data line by line (the one-dimensional data) because this can detect subject movement more accurately.

Further, CT images or tomosynthesis images can be generated by: obtaining and collecting a plurality of moire data by performing fringe scanning multiple times while changing the angle of the radiation source 11 (X-ray tube) to a subject; and performing reconstruction on the data. However, subject movement can also be detected in the data of the different angles by the method described in the embodiment.

Further, in the above embodiment, three types of reconstructed images are generated. However, the present invention is applicable to any radiation imaging system as long as the system can generate at least two types of reconstructed images.

Further, in the above embodiment, the radiation imaging device 1 uses three gratings. However, if coherence of X-rays is sufficient, the device 1 does not need to use the multi-slit 12. The present invention is applicable to this case too. Examples of the device which does not use the multi-slit 12 include a device using a Talbot interferometer, which is described in Reference Document 3 mentioned above.

Further, if the radiation imaging device 1 is configured to directly observe a self-image with the radiation detector 16, the self-image having the interval twice as large as the pixel size of the radiation detector 16 or more, the device 1 does not need to use the second grating 15. In this case, a differential phase image, a small-angle scattering image and an absorption image can be obtained by taking a plurality of images of the self-image and performing calculation based on the principles of fringe scanning from change in intensity of the self-image. The self-image having the interval twice as large as the pixel size or more and moire fringes as an envelope of a self-image having the interval smaller than the pixel size and the interval of the second grating 15 are substantially the same, and accordingly they are the same in error and change in relationship between the images due to subject movement. Hence, the present invention is also applicable to a device which directly observes a self-image (s).

Further, the radiation imaging device 1 may be configured, as described in Reference Document 7 (Japanese Patent Application Publication No. 2012-085995), to make use of projection of an absorption grating. In this case, a differential phase image, a small-angle scattering image and an absorption image can be obtained by, using an absorption grating as the first grating 14 for example, taking a plurality of images of a fringe image having the intensity modulated by projection of the first grating 14 and performing calculation based on the principles of fringe scanning from change in intensity of the fringe image. The periodic pattern by projection of an absorption grating and the self-image by Talbot effect are affected by subject movement the same, and they are the same in mechanism of error which occurs in reconstructed images in the process of calculation based on the principles of fringe scanning. Hence, the present invention is also applicable to a device which makes use of projection of an absorption grating. The projection image of an absorption grating, the self-image by Talbot effect and the moire fringes into which the self-image is converted by the second grating 15 are all called the periodic pattern.

In addition to the above, detailed configurations and actions of the devices or the like of the radiation imaging system can also be appropriately modified within the scope not departing from the spirit of the present invention.

What is claimed is:

1. A radiation imaging system comprising:
   a radiation imaging device which includes: at least one grating provided in an emission axis direction of radiation; and a mechanism that carries a subject in an orthogonal direction which is at right angles to the emission axis direction or a mechanism that moves the radiation imaging device in the orthogonal direction, and obtains a plurality of periodic pattern images while carrying the subject or moving the radiation imaging device; and
   an image processing device including:
   a reconstruction unit which generates at least two reconstructed images of a differential phase image, an absorption image and a small-angle scattering image based on the periodic pattern images; and
      a detection unit which (i) performs regression analysis on signal values of at least two images of (a) the differential phase image, a differential absorption image generated by differentiating the absorption image, and a differential small-angle scattering image generated by differentiating the small-angle scattering image, or (b) a phase image generated by integrating the differential phase image, the absorption image, and the small-angle scattering image, the at least two images being a target of the regression analysis, (ii) calculates an indicator value of an indicator indicating a relationship between the at least two images, and (iii) detects image quality deterioration due to change in relative position of the radiation imaging device and the subject based on the calculated indicator value.

2. The radiation imaging system according to claim 1, wherein the detection unit (i) performs, as the regression analysis, simple regression analysis on at least one image combination, treating two images of (a) the differential phase image, the differential absorption image and the differential small-angle scattering image or (b) the phase image, the absorption image and the small-angle scattering image as one image combination, and (ii) calculates the indicator value of the indicator indicating the relationship between the at least two images.

3. The radiation imaging system according to claim 1, wherein the detection unit (i) performs, as the regression analysis, multiple regression analysis on three images of (a) the differential phase image, the differential absorption image and the differential small-angle scattering image or (b) the phase image, the absorption image and the small-angle scattering image as one image combination, and (ii) calculates, as the indicator value of the indicator indicating the relationship between the at least two images, an indicator value of an indicator indicating a relationship between the three images.

4. The radiation imaging system according to claim 1, wherein the indicator is one or a plurality of a coefficient of regression, a coefficient of determination, a standard deviation from a regression equation, a coefficient of correlation, and an error from the regression equation.

5. The radiation imaging system according to claim 1, wherein the detection unit (i) stores in advance an indicator value of the indicator obtained from image data having no change in relative position of the radiation imaging device and the subject as a reference value, and (ii) detects the image quality deterioration based on a difference between the calculated indicator value and the reference value or based on a change rate obtained by dividing the calculated indicator value by the reference value.

6. The radiation imaging system according to claim 1, further comprising an extraction unit which, if the subject is a human body, extracts a pixel of a bone part from the images which are the target of the regression analysis, wherein
   the detection unit performs the regression analysis, using only data of the extracted pixel of the bone part.

7. The radiation imaging system according to claim 1, further comprising a pre-processing unit which performs, before the regression analysis, a binning process or a filtering process on the images which are the target of the regression analysis.

8. The radiation imaging system according to claim 1, further comprising a noise pixel extraction unit which extracts a noise pixel from the images which are the target of the regression analysis, wherein
   the detection unit excludes the extracted noise pixel from the target of the regression analysis.

9. The radiation imaging system according to claim 1, further comprising an output unit which outputs a warning when the detection unit detects the image quality deterioration.

10. An image processing device which performs image processing on a plurality of periodic pattern images obtained by a radiation imaging device which includes at least one grating provided in an emission axis direction of radiation and a mechanism that carries a subject in an orthogonal direction which is at right angles to the emission axis direction or a mechanism that moves the radiation imaging device in the orthogonal direction while carrying the subject or moving the grating, the image processing device comprising:
   a reconstruction unit which generates at least two reconstructed images of a differential phase image, an absorption image and a small-angle scattering image based on the periodic pattern images; and a detection unit which (i) performs regression analysis on signal values of at least two images of (a) the differential phase image, a differential absorption image generated by differentiating the absorption image, and a differential small-angle scattering image generated by differentiating the small-angle scattering image, or (b) a phase image generated by integrating the differential phase image, the absorption image, and the small-angle scattering image, (ii) calculates an indicator value of an indicator indicating a relationship between the at least two images, and (iii) detects image quality deterioration due to change in relative position of the radiation imaging device and the subject based on the calculated indicator value.

* * * * *